(12) United States Patent
Verkman et al.

(10) Patent No.: US 7,696,244 B2
(45) Date of Patent: Apr. 13, 2010

(54) COMPOUNDS HAVING ACTIVITY IN INCREASING ION TRANSPORT BY MUTANT-CFTR AND USES THEREOF

(75) Inventors: Alan Verkman, San Francisco, CA (US); Luis J. V. Galietta, San Francisco, CA (US); R. Kiplin Guy, Concord, CA (US)

(73) Assignee: The Regents of the University of California, Oakland, CA (US)

( * ) Notice: Subject to any disclaimer, the term of this patent is extended or adjusted under 35 U.S.C. 154(b) by 36 days.

(21) Appl. No.: 10/556,195

(22) PCT Filed: May 14, 2004

(86) PCT No.: PCT/US2004/015386

§ 371 (c)(1),
(2), (4) Date: Mar. 20, 2007

(87) PCT Pub. No.: WO2004/110352

PCT Pub. Date: Dec. 23, 2004

(65) Prior Publication Data

US 2007/0265316 A1 Nov. 15, 2007

Related U.S. Application Data

(60) Provisional application No. 60/471,060, filed on May 16, 2003.

(51) Int. Cl.
*A61K 31/38* (2006.01)
*A01N 43/06* (2006.01)
*A01N 43/12* (2006.01)

(52) U.S. Cl. .................. 514/447; 514/443; 514/445

(58) Field of Classification Search .................. 514/443, 514/445, 447
See application file for complete search history.

(56) References Cited

U.S. PATENT DOCUMENTS 5,747,518 A 5/1998 Yoshikawa et al.
6,414,013 B1 7/2002 Fancelli et al.

FOREIGN PATENT DOCUMENTS

WO WO03104219 A1 12/2003

OTHER PUBLICATIONS

Hartman et al. ("4-substituted thiophene- and furan-2-sulfonamides as topical carbonic anhydrase inhibitors."; J Med Chem. Oct. 16, 1992;35(21):3822-31.*
Freshney (Culture of Animal Cells, A Manual of Basic Technique, Alan R. Liss, Inc., 1983, New York, p. 4).*
Dermer (Bio/Technology, 1994, 12:320).*
Devor et al. (Am J Physiol Cell Physiol (2000); 279:C461-79).*
Yang et al., "Nanomolar Affinity Small Molecule Correctors of Defective delta-F508-CFTR Chloride Channel Gating", The Journal of Biological Chemistry; vol. 278, No. 37, Issue of Sep. 12, 2003: pp. 35079-35085.*
Brown, et al., "Chemical chaperones correct the mutant phenotype of the F508 cystic fibrosis transmembrane conductance regulator protein," (1996) Cell Stress & Chaperones 1, 117-125.
Dalemans et al., "Altered chloride ion channel kinetics associated with the F508 cystic fibrosis mutation," (1991) Nature 354, 526-528.
Denning et al., "Processing of mutant cystic fibrosis transmembrane conductance regulator is temperature-sensitive," (1992) Nature 358, 761-764.
Drumm et al., "Chloride Conductance Expressed by F508 and Other Mutant CFTRs in Xenopus Oocytes," (1991) Science 254, 1797-1799.
Egan et al., "Calcium-pump inhibitors induce functional surface expression of F508-CFTR protein in cystic fibrosis epithelial cells," (2002) Nature Med. 8, 485-492.
Egan et al., "Curcumin, a Major Constituent of Turmeric, Corrects Cystic Fibrosis Defects," (2004) Science 304:600-60.
Haws et al., "F508-CFTR channels: kinetics, activation by foskolin, and potentiation by xanthines," (1996) Am. J. Physiol. 270, C1544-C1555.
Hwang et al., "Genistein potentiates wild-type and F508-CFTR channel activity," (1997) Am. J. Physiol. 273, C988-C998.
Kang et al., "Life extension in Drosophila by feeding a drug," (2002) Proc. Natl. Acad. Sci. U.S.A. 99, 838-843.
Rubenstein et al., "Sodium 4-phenylbutyrate downregulates Hsc70: implications for intracellular trafficking of F508-CFTR," (2000) Am. J. Physiol. 278, C259-C267.
Sato et al., "Glycerol Reverses the Misfolding Phenotype of the Most Common Cystic Fibrosis Mutation*," (1996) J. Biol. Chem. 271, 635-638.
Sharma et al., "Conformational and Temperature-sensitive Stability Defects of the F508 Cystic Fibrosis Transmembrane Conductance Regulator in Post-endoplasmic Reticulum Compartments*," (2001) J. Biol. Chem. 276, 8942-8950.
Wang et al., "Deletion of phenylalanine 508 causes attenuated phosphorylation-dependent activation of CFTR chloride channels," (2000) J. Physiol. 524, 637-638.

* cited by examiner

*Primary Examiner*—Frederick Krass
*Assistant Examiner*—Chris E Simmons
(74) *Attorney, Agent, or Firm*—Carol L. Francis; Bozicevic, Field & Francis, LLP

(57) ABSTRACT

The invention provides compositions, including pharmaceutical preparations, which comprise one or more substituted thiophene, benzofuran, pyrimidinetrione, dihydropyridine, tetrahydrocarbazol or anthraquinone compounds. The invention also features methods of use of such compositions in increasing activity of mutant-cystic fibrosis transmembrane conductance regulator protein in a cell, e.g. by increasing ion transport in a mutant-CFTR.

28 Claims, 26 Drawing Sheets

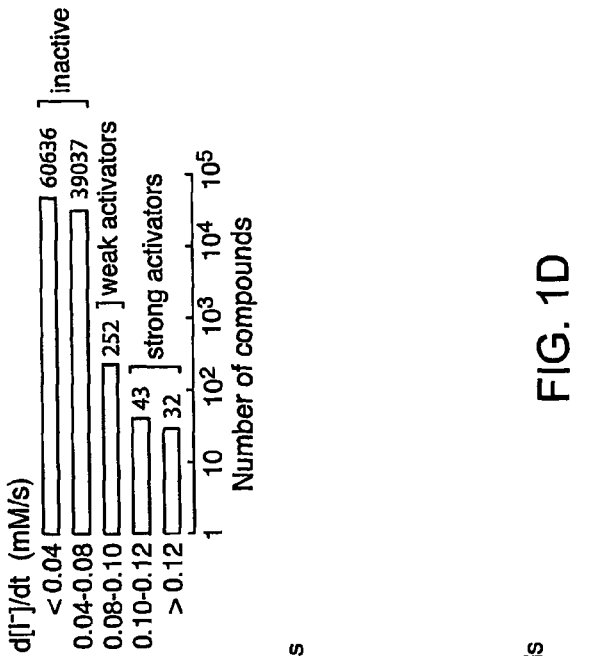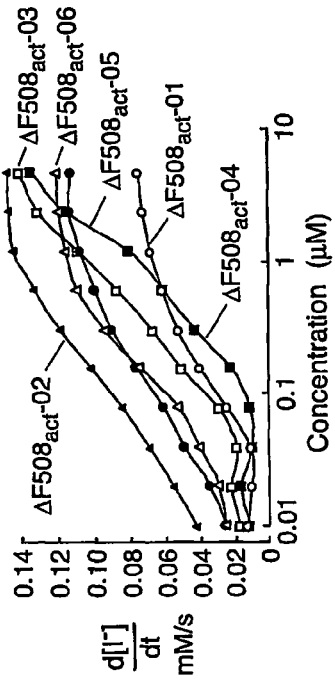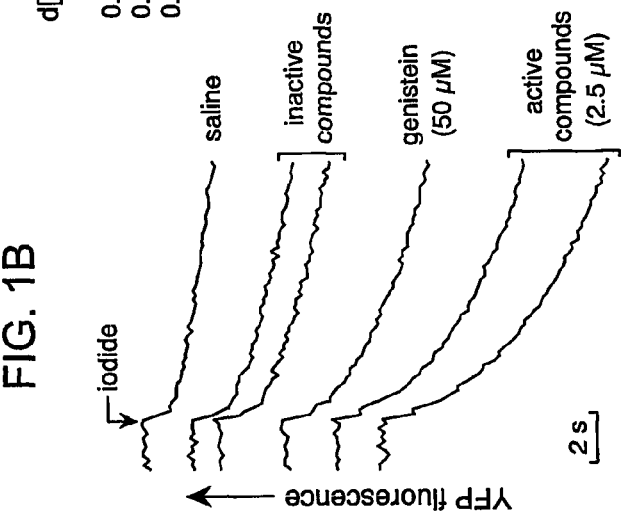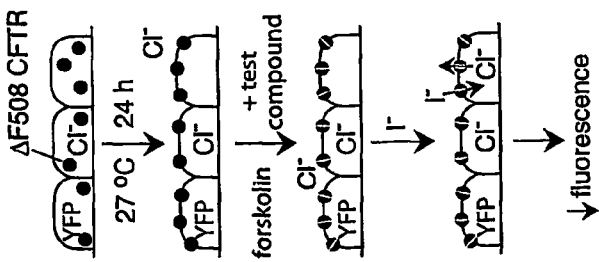

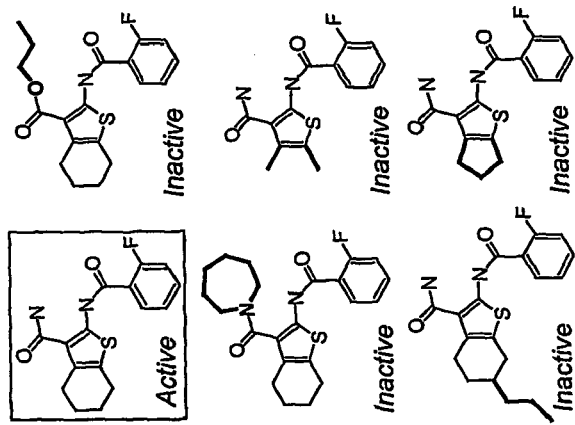
FIG. 5A
FIG. 5B
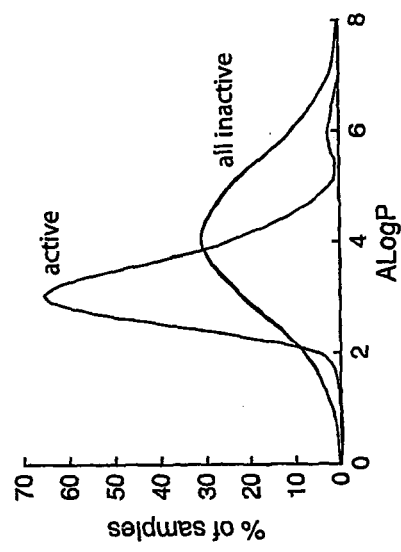
FIG. 5C
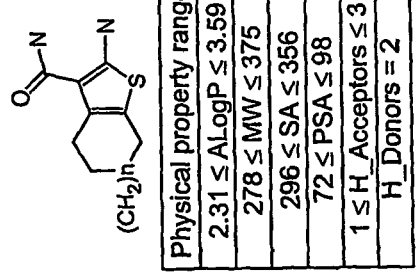
FIG. 5D
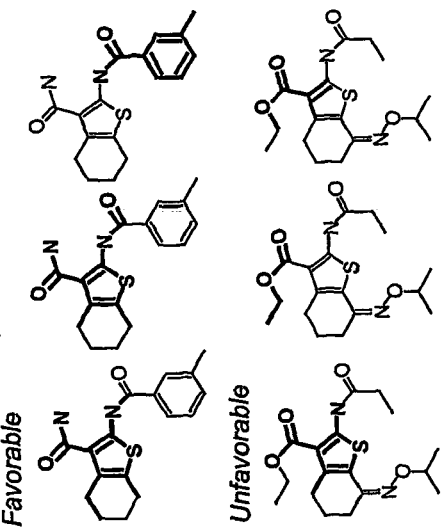
FIG. 5E
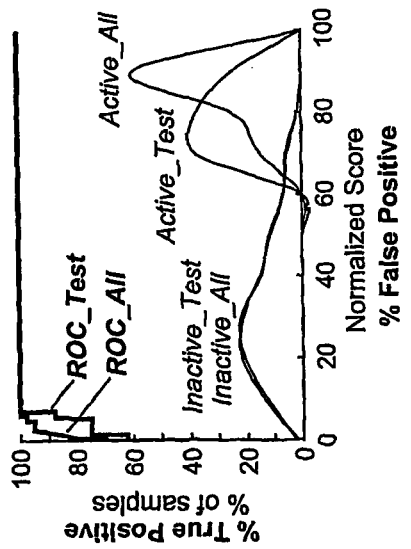

| ID | IDNUMBER | structure | fmla structure | mol weight structure | cluster | cluster span | logp | logd | logsw | Vmax | Kd | good moderate |
|---|---|---|---|---|---|---|---|---|---|---|---|---|
| 4438 | 8010-4085 | 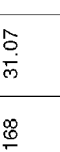 | C19H17F6N3O3S | 481.42004 | 333096 | 1 | 5.1305 | 4.6769 | -4.2168 | 31.07 | 0.9314 | |
| 4436 | 8009-6115 | 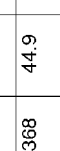 | C16H15FN2O2S | 318.37255 | 21001 | 10 | 3.1792 | 3.1859 | -3.2368 | 44.9 | 0.209 | Good |
| 4337 | 1000-0685 | 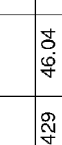 | C16H15N3O4S | 345.37965 | 10602 | 12 | 2.8681 | 2.69328 | -2.57429 | 46.04 | 0.558 | Good |
| 4331 | 1000-0653 | 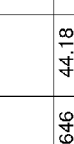 | C14H20N2O2S | 280.3917 | 20999 | 19 | 2.8887 | 3.2206 | -1.43646 | 44.18 | 0.2432 | Good |
| 4332 | 1000-0654 | 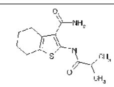 | C13H18N2O2S | 266.36461 | 20999 | 19 | 2.4388 | 2.3762 | -2.82498 | 47.33 | 0.8334 | Good |
| 4414 | 3772-2823 | 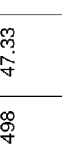 | C16H22N2O2S | 306.42994 | 20999 | 19 | 3.4358 | 3.5128 | -2.58419 | 45.33 | 0.1203 | Good |
| 4415 | 3772-3510 | 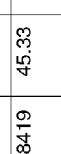 | C17H17N3O4S | 359.40674 | 10602 | 12 | 3.3543 | 2.2694 | 0.74472 | 42.53 | 0.097 | Good |
| 4416 | 3772-3765 | 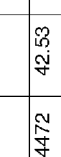 | C16H15ClN2O2S | 334.82715 | 21006 | 7 | 3.6381 | 3.8343 | -3.9393 | 45.91 | 2.469 | Good |
FIG. 6

| ID | IDNUMBER | structure | fmla structure | mol weight structure | cluster | cluster span | logp | logd | logsw | Vmax | Kd | good moderate |
|---|---|---|---|---|---|---|---|---|---|---|---|---|
| 4417 | 3772-3894 | 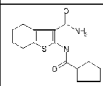 | C15H20N2O2S | 292.40285 | 20999 | 19 | 2.9796 | 3.4156 | -2.35246 | 39.98 | 0.7156 | |
| 4406 | 3759-1252 | 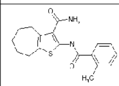 | C18H20N2O2S | 328.4363 | 61838 | 24 | 3.9161 | 2.42422 | -1.34608 | 36.29 | 0.4211 | Good |
| 4420 | 3992-2143 | 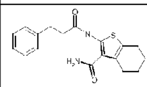 | C18H20N2O2S | 328.4363 | 20999 | 19 | 3.4647 | 3.4502 | -1.1254 | 47.18 | 0.1851 | Good |
| 4421 | 4227-2964 | 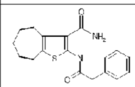 | C18H20N2O2S | 328.4363 | 159948 | 1 | 3.4647 | 3.3775 | -3.8378 | 40.04 | 0.6091 | Good |
| 4364 | 2425-4463 | 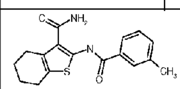 | C17H18N2O2S | 314.40921 | 21010 | 11 | 3.4599 | 3.4865 | -1.86319 | 41.59 | 1.105 | Good |
| 4349 | 21159-1373 | 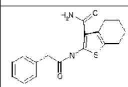 | C17H18N2O2S | 314.40921 | 61026 | 3 | 3.0085 | 3.4421 | -0.90317 | 40.75 | 0.2452 | Good |
| 4345 | 1682-7891 | 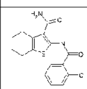 | C16H15ClN2O2S | 334.82715 | 21006 | 7 | 3.6381 | 3.4682 | -3.6912 | 40.59 | 0.2254 | Good |
| 4342 | 1488-0300 | 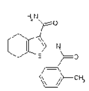 | C17H18N2O2S | 314.40921 | 21010 | 11 | 3.4599 | 1.96547 | -1.7735 | 35.34 | 0.3857 | Good |

FIG. 6 (Con't)

| ID | IDNUMBER | structure | fmla structure | mol weight structure | cluster | cluster span | logp | logd | logsw | Vmax | Kd | good moderate |
|---|---|---|---|---|---|---|---|---|---|---|---|---|
| 6595187 | 1488-0300 | 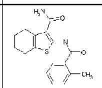 | C17H18N2O2S | 314.40921 | 21010 | 11 | 3.4599 | 1.96547 | -1.7735 | 81.4 | 0.52 | Good |
| 6595303 | 3341-1114 | 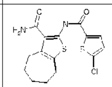 | C15H15ClN2O2S2 | 354.88 | 114469 | 4 | 4.0294 | 3.2267 | -1.91232 | 81.36 | 0.2 | Good |
| 6595357 | 8009-6049 | 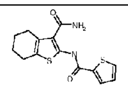 | C14H14N2O2S2 | 306.40788 | 117541 | 20 | 2.6996 | 3.3151 | -1.87544 | 82.03 | 1.01 | Good |
| 6595174 | 0973-0021 | 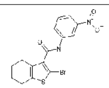 | C15H13BrN2O3S | 381.25046 | 19933 | 7 | 4.3094 | 5.3471 | -4.4743 | | | moderate |
| 6595203 | 2303-0608 | 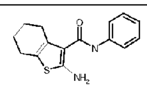 | C15H16N2OS | 272.37157 | 69549 | 12 | 3.2249 | 3.2413 | -3.6023 | | | moderate |
| 6595246 | 2556-0261 | 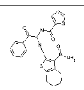 | C22H21N3O3S2 | 439.55897 | 78645 | 1 | 3.9768 | 2.4005 | -0.041458 | | | moderate |
| 6595293 | 3261-0996 | 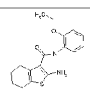 | C17H20N2O2S | 316.42515 | 76627 | 11 | 3.5573 | 4.4389 | -4.4043 | | | moderate |
| 6595294 | 3261-1013 | 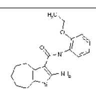 | C18H22N2O2S | 330.45224 | 61836 | 11 | 4.0135 | 5.1922 | -4.5155 | | | moderate |

FIG. 6 (Con't)

| ID | IDNUMBER | structure | fmla structure | mol weight structure | cluster | cluster span | logp | logd | logsw | Vmax | Kd | good moderate |
|---|---|---|---|---|---|---|---|---|---|---|---|---|
| 6595295 | 3261-1088 | 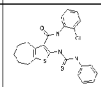 | C23H22ClN3OS2 | 456.03229 | 106166 | 1 | 7.0731 | 6.1085 | -2.44855 | | | |
| 6595296 | 3261-1112 | 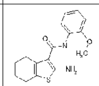 | C16H18N2O2S | 302.39806 | 76627 | 11 | 3.2085 | 3.5671 | -3.9887 | | | moderate |
| 6595317 | 3453-2120 | 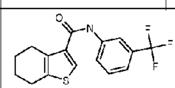 | C16H14F3NOS | 325.35528 | 19923 | 15 | 4.3747 | 5.8012 | -6.1839 | | | moderate |
| 6595339 | 4264-1174 | 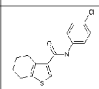 | C15H14ClNOS | 291.80193 | 19923 | 15 | 4.0968 | 5.1273 | -5.5798 | | | moderate |
| 6595356 | 8009-1054 | 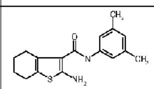 | C17H20N2OS | 300.42575 | 69549 | 12 | 4.1973 | 4.1278 | -2.13772 | | | moderate |
| 6595360 | 8009-7574 | 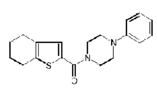 | C19H22N2OS | 326.46399 | 328479 | 2 | 4.1196 | 5.519 | -4.123 | | | moderate |
| 6595372 | 8012-4539 | 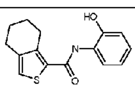 | C15H15NO2S | 273.3563 | 342410 | 28 | 3.5864 | 3.6567 | -3.9232 | | | moderate |
| 6595373 | 8012-4972 | 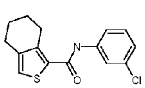 | C15H14ClNOS | 291.80193 | 342410 | 28 | 4.5182 | 5.2413 | -4.6639 | | | moderate |

FIG. 6 (Con't)

| ID | IDNUMBER | structure | fmla structure | mol weight structure | cluster | cluster span | logp | logd | logsw | Vmax | Kd | good moderate |
|---|---|---|---|---|---|---|---|---|---|---|---|---|
| 6595378 | 8012-6952 | 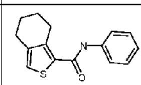 | C15H15NOS | 257.3569 | 342410 | 28 | 3.8538 | 3.8581 | -4.7437 | | | moderate |
| 6595385 | 8012-8301 | 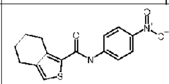 | C15H14N2O3S | 302.35443 | 345507 | 2 | 3.7482 | 4.5592 | -4.7503 | | | moderate |
| 6595161 | 0973-0005 | 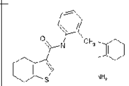 | C16H17NOS | 271.38399 | 19923 | 15 | 3.9186 | 3.713 | -3.3695 | | | |
| 6595162 | 0973-0006 | 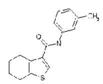 | C16H17NOS | 271.38399 | 19923 | 15 | 3.9186 | 4.179 | -5.5601 | | | inactive |
| 6595163 | 0973-0007 | 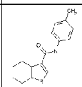 | C16H17NOS | 271.38399 | 19923 | 15 | 3.9186 | 4.4277 | -5.4665 | | | inactive |
| 6595164 | 0973-0008 | 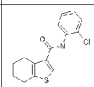 | C15H14ClNOS | 291.80193 | 19923 | 15 | 4.0968 | 4.8175 | -3.9458 | | | inactive |
| 6595165 | 0973-0009 | 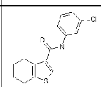 | C15H14ClNOS | 291.80193 | 19923 | 15 | 4.0968 | 5.0766 | -4.5062 | | | inactive |
| 6595166 | 0973-0011 | 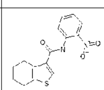 | C15H14N2O3S | 302.35443 | 19930 | 3 | 3.3268 | 4.5148 | -5.1811 | | | inactive |

FIG. 6 (Con't)

| ID | IDNUMBER | structure | fmla structure | mol weight structure | cluster | cluster span | logp | logd | logsw | Vmax | Kd | good moderate |
|---|---|---|---|---|---|---|---|---|---|---|---|---|
| 6595167 | 0973-0012 | 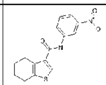 | C15H14N2O3S | 302.35443 | 19930 | 3 | 3.3268 | 4.7659 | -6.0673 | | | |
| 6595168 | 0973-0013 | 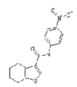 | C15H14N2O3S | 302.35443 | 19930 | 3 | 3.3268 | 4.3945 | -4.992 | | | inactive |
| 6595169 | 0973-0015 | 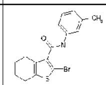 | C16H16BrNOS | 350.28002 | 19933 | 7 | 4.9012 | 4.9454 | -5.3254 | | | inactive |
| 6595170 | 0973-0016 | 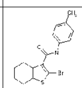 | C16H16BrNOS | 350.28002 | 19933 | 7 | 4.9012 | 4.8482 | -5.7005 | | | inactive |
| 6595171 | 0973-0017 | 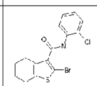 | C15H13BrClNOS | 370.69796 | 19933 | 7 | 5.0794 | 5.4192 | -7.4328 | | | inactive |
| 6595172 | 0973-0018 | 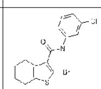 | C15H13BrClNOS | 370.69796 | 19933 | 7 | 5.0794 | 5.7806 | -6.2175 | | | inactive |
| 6595173 | 0973-0019 | 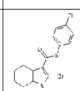 | C15H13BrClNOS | 370.69796 | 19933 | 7 | 5.0794 | 5.4028 | -6.1417 | | | inactive |
| 6595175 | 0973-0022 | 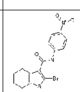 | C15H13BrN2O3S | 381.25046 | 19933 | 7 | 4.3094 | 5.0298 | -5.6865 | | | inactive |

FIG. 6 (Con't)

| ID | IDNUMBER | structure | fmla structure | mol weight structure | cluster | cluster span | logp | logd | logsw | Vmax | Kd | good moderate |
|---|---|---|---|---|---|---|---|---|---|---|---|---|
| 6595186 | 1110-0045 | 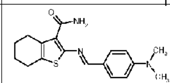 | C18H21N3OS | 327.45157 | 23001 | 1 | 3.9477 | 3.7653 | -2.02739 | | | |
| 6595188 | 1611-4913 | 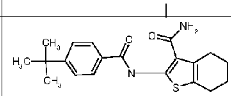 | C20H24N2O2S | 356.49048 | 21010 | 11 | 4.3741 | 4.4492 | -3.7503 | | | inactive |
| 6595189 | 1630-1141 | 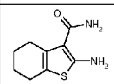 | C9H12N2OS | 196.27279 | 37242 | 5 | 1.4424 | 1.10764 | -4.2907 | | | inactive |
| 6595196 | 2169-0032 | 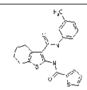 | C21H20N2O2S2 | 396.53375 | 61819 | 9 | 4.9683 | 3.5057 | -3.8856 | | | inactive |
| 6595198 | 2169-0058 | 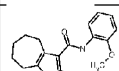 | C17H20N2O2S | 316.42515 | 61836 | 11 | 3.6647 | 4.0259 | -4.6661 | | | inactive |
| 6595202 | 2303-0607 | 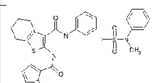 | C20H18N2O3S | 366.44206 | 61825 | 16 | 3.5963 | 2.99851 | -2.7647 | | | inactive |
| 6595204 | 2303-0610 | 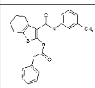 | C24H24N2O2S | 404.53508 | 69546 | 13 | 5.2772 | 4.1006 | -3.6654 | | | inactive |
| 6595205 | 2303-0611 | 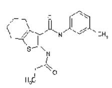 | C19H22N2O2S | 342.46339 | 69542 | 40 | 4.245 | 3.478 | -2.57264 | | | inactive |

FIG. 6 (Con't)

| ID | IDNUMBER | structure | fmla structure | mol weight structure | cluster | cluster span | logp | logd | logsw | Vmax | Kd | good moderate |
|---|---|---|---|---|---|---|---|---|---|---|---|---|
| 6595206 | 2303-0612 | 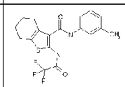 | C18H17F3N2O2S | 382.40759 | 69542 | 40 | 4.6663 | 4.4287 | -3.5414 | | | |
| 6595207 | 2303-0617 | 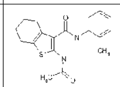 | C18H20N2O2S | 328.4363 | 69542 | 40 | 3.5781 | 2.47691 | -1.67409 | | | inactive |
| 6595208 | 2303-0618 | 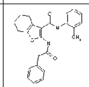 | C24H24N2O2S | 404.53508 | 69546 | 13 | 5.2772 | 4.2033 | -3.1947 | | | inactive |
| 6595209 | 2303-0627 | 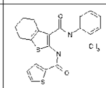 | C21H20N2O2S2 | 396.53375 | 61819 | 9 | 4.9683 | 3.8024 | -3.7599 | | | inactive |
| 6595210 | 2303-0631 | 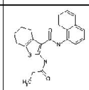 | C22H22N2O2S | 378.49684 | 69542 | 40 | 4.6672 | 3.8268 | -1.7463 | | | inactive |
| 6595213 | 2303-0643 | 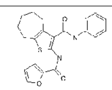 | C21H20N2O3S | 380.46915 | 61835 | 16 | 4.0525 | 3.1724 | -3.4156 | | | inactive |
| 6595214 | 2333-0632 | 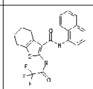 | C21H17F3N2O2S | 418.44104 | 69542 | 40 | 5.0885 | 4.5748 | -5.4814 | | | inactive |
| 6595216 | 2333-0642 | 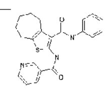 | C22H21N3O2S | 391.49557 | 66342 | 26 | 4.0618 | 2.77384 | -2.3551 | | | inactive |

FIG. 6 (Con't)

| ID | IDNUMBER | structure | fmla structure | mol weight structure | cluster | cluster span | logp | logd | logsw | Vmax | Kd | good moderate |
|---|---|---|---|---|---|---|---|---|---|---|---|---|
| 6595220 | 2411-0654 | 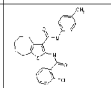 | C24H23ClN2O2S | 438.98011 | 71276 | 26 | 6.363 | 5.3547 | -5.7834 | | | |
| 6595225 | 2432-4459 | 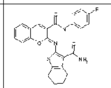 | C25H20FN3O3S | 461.51885 | 75354 | 9 | 5.0463 | 3.8243 | -1.76117 | | | inactive |
| 6595226 | 2432-4473 | 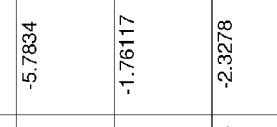 | C26H20F3N3O3S | 511.5268 | 75354 | 9 | 5.7831 | 5.5233 | -2.3278 | | | inactive |
| 6595227 | 2501-0800 | 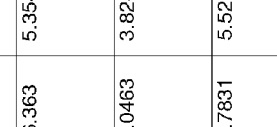 | C17H20N2O2S | 316.42515 | 76627 | 11 | 3.5573 | 4.1503 | -3.4824 | | | inactive |
| 6595229 | 2501-0823 | 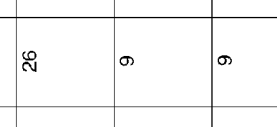 | C25H26N2O2S | 418.56217 | 76637 | 7 | 5.7334 | 4.6099 | -4.1828 | | | inactive |
| 6595230 | 2501-0824 | 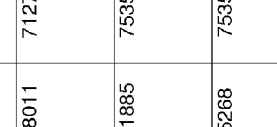 | C25H26N2O2S | 418.56217 | 76637 | 7 | 5.7334 | 4.4788 | -3.7122 | | | inactive |
| 6595231 | 2501-0826 | 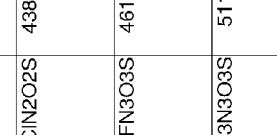 | C25H26N2O3S | 434.56157 | 61833 | 21 | 5.5448 | 4.756 | -2.61915 | | | inactive |
| 6595233 | 2501-0829 | 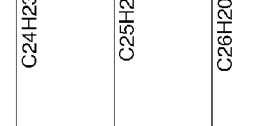 | C23H20Cl2N2O2S | 459.39805 | 71276 | 26 | 6.5412 | 5.3709 | -5.7926 | | | inactive |
FIG. 6 (Con't)

| ID | IDNUMBER | structure | fmla structure | mol weight structure | cluster | cluster span | logp | logd | logsw | Vmax | Kd | good moderate |
|---|---|---|---|---|---|---|---|---|---|---|---|---|
| 6595234 | 2501-0838 | 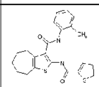 | C22H22N2O2S2 | 410.56084 | 71278 | 7 | 5.4245 | 4.2621 | -3.1695 | | | inactive |
| 6595235 | 2501-0839 | 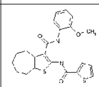 | C22H22N2O3S2 | 426.56024 | 76653 | 12 | 4.9219 | 4.805 | -2.73446 | | | inactive |
| 6595236 | 2501-0840 | 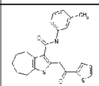 | C22H22N2O2S2 | 410.56084 | 71278 | 7 | 5.4245 | 3.9644 | -4.12 | | | inactive |
| 6595237 | 2501-0844 | 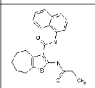 | C23H24N2O2S | 392.52393 | 76636 | 15 | 5.1234 | 4.2956 | -2.74314 | | | inactive |
| 6595238 | 2501-0845 | 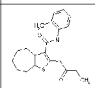 | C20H24N2O2S | 356.49048 | 76636 | 15 | 4.7012 | 3.4354 | -3.6648 | | | inactive |
| 6595239 | 2501-0846 | 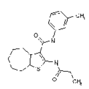 | C20H24N2O2S | 356.49048 | 76636 | 15 | 4.7012 | 3.2477 | -4.4448 | | | inactive |
| 6595240 | 2501-0856 | 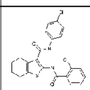 | C22H18Cl2N2O2S | 445.37096 | 51056 | 28 | 6.085 | 5.0676 | -5.5687 | | | inactive |
| 6595241 | 2501-0858 | 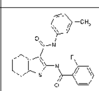 | C23H21FN2O2S | 408.49842 | 51056 | 28 | 5.4479 | 3.9713 | -4.3616 | | | inactive |

FIG. 6 (Con't)

| ID | IDNUMBER | structure | fmla structure | mol weight structure | cluster | cluster span | logp | logd | logsw | Vmax | Kd | good moderate |
|---|---|---|---|---|---|---|---|---|---|---|---|---|
| 6595242 | 2501-0860 | 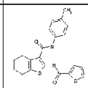 | C21H20N2O2S2 | 396.53375 | 61819 | 9 | 4.9683 | 3.4311 | -1.70135 | | | |
| 6595243 | 2513-0283 | 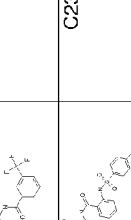 | C17H15F3N2O2S | 368.3805 | 21010 | 11 | 3.916 | 3.4808 | -3.5394 | | | inactive |
| 6595244 | 2513-0548 | 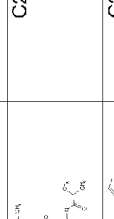 | C23H23N3O4S2 | 469.58546 | 20913 | 33 | 3.9476 | 4.3724 | -4.4224 | | | inactive |
| 6595249 | 3237-1426 | 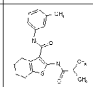 | C20H24N2O2S | 356.49048 | 69542 | 40 | 4.7075 | 3.9865 | -4.7497 | | | inactive |
| 6595251 | 3261-0004 | 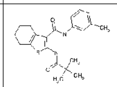 | C21H26N2O2S | 370.51757 | 69542 | 40 | 5.1244 | 4.5039 | -5.1164 | | | inactive |
| 6595254 | 3261-0246 | 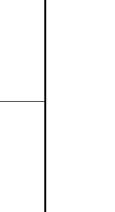 | C23H21ClN2O2S | 424.95302 | 69546 | 13 | 5.4554 | 5.3098 | -4.255 | | | inactive |
| 6595255 | 3261-0251 | 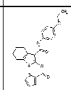 | C22H22N2O3S2 | 426.56024 | 74703 | 26 | 4.8145 | 4.8701 | -2.51499 | | | inactive |
| 6595257 | 3261-0266 | 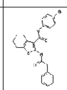 | C23H21BrN2O2S | 469.40402 | 69546 | 13 | 5.5394 | 4.6757 | -3.8216 | | | inactive |
FIG. 6 (Con't)

| ID | IDNUMBER | structure | fmla structure | mol weight structure | cluster | cluster span | logp | logd | logsw | Vmax | Kd | good moderate |
|---|---|---|---|---|---|---|---|---|---|---|---|---|
| 6595258 | 3261-0269 | 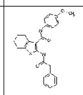 | C24H24N2O3S | 420.53448 | 76663 | 13 | 4.7746 | 5.0405 | -2.9798 | | | |
| 6595259 | 3261-0279 | 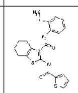 | C21H20N2O3S2 | 412.53315 | 74703 | 26 | 4.4657 | 4.4128 | -1.83868 | | | inactive |
| 6595260 | 3261-0327 | 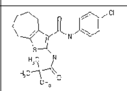 | C21H25ClN2O2S | 404.9626 | 76636 | 15 | 5.7588 | 6.6114 | -4.583 | | | inactive |
| 6595261 | 3261-0344 | 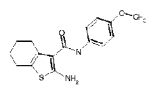 | C16H18N2O2S | 302.39806 | 76627 | 11 | 3.2085 | 3.8247 | -3.7141 | | | inactive |
| 6595263 | 3261-0358 | 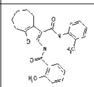 | C25H26N2O2S | 418.56217 | 71276 | 26 | 6.1848 | 4.5955 | -4.3431 | | | inactive |
| 6595267 | 3261-0701 | 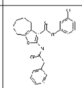 | C24H23ClN2O2S | 438.98011 | 76637 | 7 | 5.9116 | 6.2422 | -4.6084 | | | inactive |
| 6595268 | 3261-0713 | 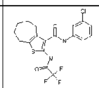 | C18H16ClF3N2O2S | 416.85262 | 69562 | 10 | 5.3007 | 4.9593 | -6.173 | | | inactive |
| 6595269 | 3261-0728 | 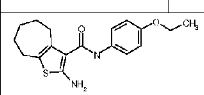 | C18H22N2O2S | 330.45224 | 61836 | 11 | 4.0135 | 4.7751 | -2.98694 | | | inactive |

FIG. 6 (Con't)

| ID | IDNUMBER | structure | fmla structure | mol weight structure | cluster | cluster span | logp | logd | logsw | Vmax | Kd | good moderate |
|---|---|---|---|---|---|---|---|---|---|---|---|---|
| 6595272 | 3261-0740 | 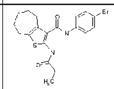 | C19H21BrN2O2S | 421.35942 | 105927 | 1 | 4.9634 | 5.543 | -3.6267 | | | |
| 6595276 | 3261-0762 | 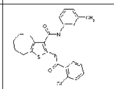 | C24H23ClN2O2S | 438.98011 | 71276 | 26 | 6.363 | 5.5541 | -5.8115 | | | inactive |
| 6595277 | 3261-0774 | 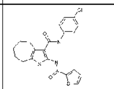 | C21H19ClN2O2S2 | 430.97878 | 71278 | 7 | 5.6027 | 5.4697 | -3.3742 | | | inactive |
| 6595278 | 3261-0778 | 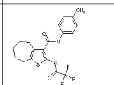 | C19H19F3N2O2S | 396.43468 | 69562 | 10 | 5.1225 | 4.3401 | -3.9653 | | | inactive |
| 6595279 | 3261-0779 | 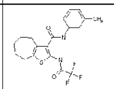 | C19H19F3N2O2S | 396.43468 | 69562 | 10 | 5.1225 | 3.8394 | -4.0589 | | | inactive |
| 6595281 | 3261-0787 | 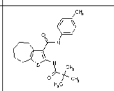 | C22H28N2O2S | 384.54466 | 76636 | 15 | 5.5806 | 4.9439 | -4.4625 | | | inactive |
| 6595282 | 3261-0788 | 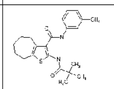 | C22H28N2O2S | 384.54466 | 76636 | 15 | 5.5806 | 4.9627 | -4.9902 | | | inactive |
| 6595283 | 3261-0789 | 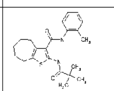 | C22H28N2O2S | 384.54466 | 76636 | 15 | 5.5806 | 5.2304 | -5.0246 | | | inactive |

FIG. 6 (Con't)

| ID | IDNUMBER | structure | fmla structure | mol weight structure | cluster | cluster span | logp | logd | logsw | Vmax | Kd | good moderate |
|---|---|---|---|---|---|---|---|---|---|---|---|---|
| 6595284 | 3261-0813 | 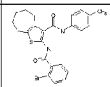 | C24H23BrN2O2S | 483.43111 | 71276 | 26 | 6.447 | 4.9614 | -3.5688 | | | |
| 6595287 | 3261-0854 | 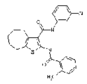 | C24H23ClN2O2S | 438.98011 | 71276 | 26 | 6.363 | 6.0855 | -5.8175 | | | inactive |
| 6595288 | 3261-0883 | 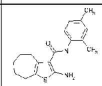 | C18H22N2OS | 314.45284 | 61836 | 11 | 4.6535 | 4.5004 | -3.1628 | | | inactive |
| 6595289 | 3261-0889 | 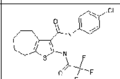 | C18H16ClF3N2O2S | 416.85262 | 69562 | 10 | 5.3007 | 5.1503 | -6.3958 | | | inactive |
| 6595297 | 3261-1121 | 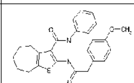 | C25H26N2O3S | 434.56157 | 105908 | 14 | 5.2308 | 5.799 | -2.60421 | | | inactive |
| 6595300 | 3322-0450 | 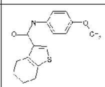 | C16H17NO2S | 287.38339 | 19923 | 15 | 3.416 | 4.6328 | -5.253 | | | inactive |
| 6595309 | 3367-1129 | 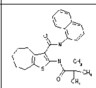 | C25H28N2O2S | 420.57811 | 76636 | 15 | 6.0028 | 6.0481 | -7.3245 | | | inactive |
| 6595311 | 3453-2103 | 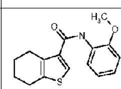 | C16H17NO2S | 287.38339 | 19923 | 15 | 3.416 | 4.159 | -5.1736 | | | inactive |

FIG. 6 (Con't)

| ID | IDNUMBER | structure | fmla structure | mol weight structure | cluster | cluster span | logp | logd | logsw | Vmax | Kd | good moderate |
|---|---|---|---|---|---|---|---|---|---|---|---|---|
| 6595313 | 3453-2115 | 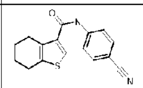 | C16H14N2OS | 282.36678 | 19923 | 15 | 3.3113 | 4.0759 | -4.4105 | | | |
| 6595314 | 3453-2117 | 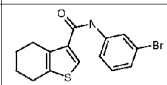 | C15H14BrNOS | 336.25293 | 19923 | 15 | 4.1808 | 5.8466 | -5.7932 | | | inactive |
| 6595315 | 3453-2118 | 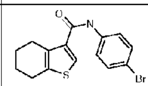 | C15H14BrNOS | 336.25293 | 19923 | 15 | 4.1808 | 5.7182 | -5.8126 | | | inactive |
| 6595316 | 3453-2119 | 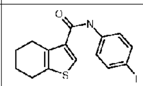 | C15H14FNOS | 275.34733 | 19923 | 15 | 3.6379 | 5.1899 | -6.2309 | | | inactive |
| 6595322 | 3759-1370 | 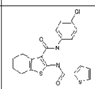 | C20H17ClN2O2S2 | 416.95169 | 61819 | 9 | 5.1465 | 5.3287 | -3.895 | | | inactive |
| 6595324 | 3759-1406 | 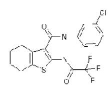 | C17H14ClF3N2O2S | 402.82553 | 69542 | 40 | 4.8445 | 5.2639 | -5.1822 | | | inactive |
| 6595325 | 3759-1444 | 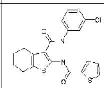 | C20H17ClN2O2S2 | 416.95169 | 61819 | 9 | 5.1465 | 5.549 | -4.3092 | | | inactive |
| 6595327 | 3759-1448 | 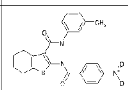 | C23H21N3O4S | 435.50552 | 69557 | 2 | 5.1368 | 2.88239 | -4.7187 | | | inactive |

FIG. 6 (Con't)

| ID | IDNUMBER | structure | fmla structure | mol weight structure | cluster | cluster span | logp | logd | logsw | Vmax | Kd | good moderate |
|---|---|---|---|---|---|---|---|---|---|---|---|---|
| 6595342 | 4488-1582 | 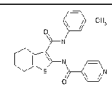 | C22H21N3O2S | 391.49557 | 117427 | 19 | 4.0918 | 2.40993 | -1.80869 | | | |
| 6595343 | 4488-1630 | 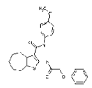 | C25H26N2O4S | 450.56097 | 105955 | 9 | 5.0313 | 5.2128 | -1.86311 | | | inactive |
| 6595344 | 4488-1670 | 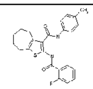 | C24H23FN2O2S | 422.52551 | 71276 | 26 | 5.9041 | 4.2816 | -3.2058 | | | inactive |
| 6595345 | 4488-1675 | 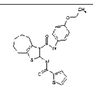 | C23H24N2O3S2 | 440.58733 | 71278 | 7 | 5.2707 | 5.5376 | -3.03246 | | | inactive |
| 6595358 | 8009-6115 | 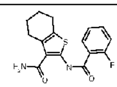 | C16H15FN2O2S | 318.37255 | 21001 | 10 | 3.1792 | 3.1859 | -3.2368 | | | inactive |
| 6595359 | 8009-6995 | 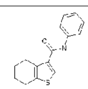 | C15H15NOS | 257.3569 | 19923 | 15 | 3.4324 | 3.6934 | -4.9854 | | | inactive |
| 6595361 | 8010-1203 | 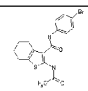 | C17H17BrN2O2S | 393.30524 | 331109 | 1 | 3.8403 | 4.2959 | -2.72591 | | | inactive |
| 6595362 | 8010-1399 | 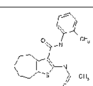 | C19H22N2O2S | 342.46339 | 76636 | 15 | 4.0343 | 2.32114 | -1.99118 | | | inactive |

FIG. 6 (Con't)

| ID | IDNUMBER | structure | fmla structure | mol weight structure | cluster | cluster span | logp | logd | logsw | Vmax | Kd | good moderate |
|---|---|---|---|---|---|---|---|---|---|---|---|---|
| 6595364 | 8010-3284 | 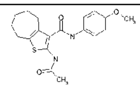 | C19H22N2O3S | 358.46279 | 76635 | 11 | 3.5317 | 3.7425 | -2.12331 | | | |
| 6595365 | 8012-3982 | 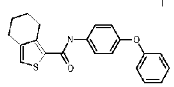 | C21H19NO2S | 349.45508 | 342410 | 28 | 5.414 | 6.5217 | -4.1301 | | | inactive |
| 6595366 | 8012-4095 | 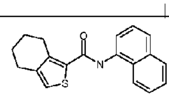 | C19H17NOS | 307.41744 | 342410 | 28 | 4.7622 | 5.6731 | -6.4353 | | | inactive |
| 6595367 | 8012-4096 | 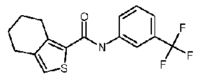 | C16H14F3NOS | 325.35528 | 342410 | 28 | 4.7961 | 5.7755 | -6.3416 | | | inactive |
| 6595368 | 8012-4098 | 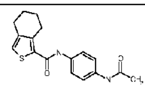 | C17H18N2O2S | 314.40921 | 342410 | 28 | 2.9742 | 2.7706 | -3.6379 | | | inactive |
| 6595369 | 8012-4099 | 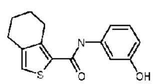 | C15H15NO2S | 273.3563 | 342410 | 28 | 3.5864 | 3.9122 | -3.6788 | | | inactive |
| 6595370 | 8012-4332 | 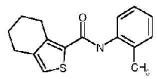 | C16H17NOS | 271.38399 | 342410 | 28 | 4.34 | 3.8375 | -3.5274 | | | inactive |
| 6595371 | 8012-4333 | 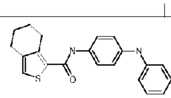 | C21H20N2OS | 348.47035 | 342410 | 28 | 5.4039 | 5.6193 | -5.3753 | | | inactive |

FIG. 6 (Con't)

| ID | IDNUMBER | structure | fmla structure | mol weight structure | cluster | cluster span | logp | logd | logsw | Vmax | Kd | good moderate |
|---|---|---|---|---|---|---|---|---|---|---|---|---|
| 6595374 | 8012-5107 | 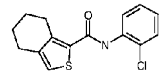 | C15H14ClNOS | 291.80193 | 342410 | 28 | 4.5182 | 4.9822 | -4.1037 | | | |
| 6595375 | 8012-5108 | 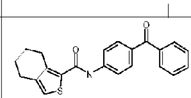 | C22H19NO2S | 361.46623 | 342410 | 28 | 5.3872 | 4.5406 | -4.0773 | | | inactive |
| 6595376 | 8012-6085 | 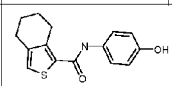 | C15H15NO2S | 273.3563 | 342410 | 28 | 3.5864 | 3.7908 | -3.9544 | | | inactive |
| 6595377 | 8012-6160 | 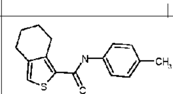 | C16H17NOS | 271.38399 | 342410 | 28 | 4.34 | 4.5924 | -5.2249 | | | inactive |
| 6595379 | 8012-7731 | 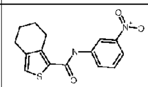 | C15H14N2O3S | 302.35443 | 345507 | 2 | 3.7482 | 5.233 | -6.2858 | | | inactive |
| 6595380 | 8012-7747 | 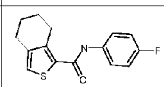 | C15H14FNOS | 275.34733 | 342410 | 28 | 4.0593 | 5.3546 | -5.9892 | | | inactive |
| 6595381 | 8012-7748 | 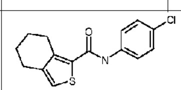 | C15H14ClNOS | 291.80193 | 342410 | 28 | 4.5182 | 5.292 | -5.7376 | | | inactive |
| 6595382 | 8012-7871 | 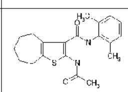 | C20H24N2O2S | 356.49048 | 76636 | 15 | 4.5205 | 2.90879 | -3.1594 | | | inactive |

FIG. 6 (Con't)

| ID | IDNUMBER | structure | fmla structure | mol weight structure | cluster | cluster span | logp | logd | logsw | Vmax | Kd | good moderate |
|---|---|---|---|---|---|---|---|---|---|---|---|---|
| 6595383 | 8012-7943 | 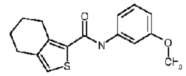 | C16H17NO2S | 287.38339 | 342410 | 28 | 3.8374 | 4.6675 | -5.116 | | | |
| 6595384 | 8012-8272 | 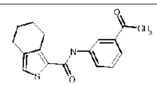 | C17H17NO2S | 299.39454 | 342410 | 28 | 3.5937 | 4.2432 | -4.5188 | | | inactive |
| 6595386 | 8012-8306 | 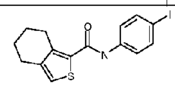 | C15H14INOS | 383.25333 | 342410 | 28 | 4.432 | 6.3646 | -5.894 | | | inactive |
| 6595387 | 8012-8872 | 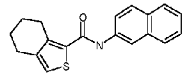 | C19H17NOS | 307.41744 | 342410 | 28 | 4.7622 | 5.811 | -6.024 | | | inactive |
| 6595388 | 8012-9353 | 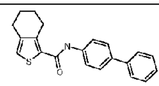 | C21H19NOS | 333.45568 | 346794 | 1 | 5.3722 | 5.3088 | -5.9195 | | | inactive |
| 6595389 | 8013-0873 | 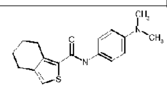 | C17H20N2OS | 300.42575 | | | 4.016 | 4.6651 | -2.52033 | | | inactive |
| 6595390 | K801-0350 | 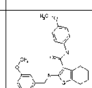 | C24H26N2O3S | 422.55042 | | | 5.053 | 4.5816 | -3.0758 | | | inactive |
| 4108 | 2303-0608 | 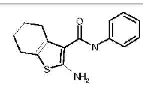 | C15H16N2OS | 272.37157 | 69549 | 12 | 3.2249 | 3.2413 | -3.6023 | | | inactive |

FIG. 6 (Con't)

| ID | IDNUMBER | structure | fmla structure | mol weight structure | cluster | cluster span | logp | logd | logsw | Vmax | Kd | good moderate |
|---|---|---|---|---|---|---|---|---|---|---|---|---|
| 4109 | 2333-0645 | 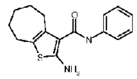 | C16H18N2OS | 286.39866 | 61836 | 11 | 3.6811 | 3.8203 | -3.5906 | | | inactive |
| 4110 | 2798-0136 | 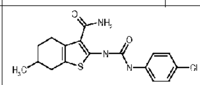 | C17H18ClN3O2S | 363.86891 | 77158 | 3 | 3.7981 | 4.6847 | -4.1095 | | | inactive |
| 4111 | 2969-0226 | 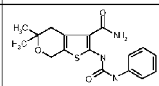 | C17H19N3O3S | 345.42328 | 87325 | 1 | 2.0379 | 3.02481 | -2.35928 | | | inactive |
| 4112 | 8002-7243 | 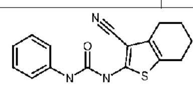 | C16H15N3OS | 297.38145 | | | 3.7586 | 3.14961 | -3.9069 | | | inactive |

FIG. 6 (Con't)

COMPOUNDS HAVING ACTIVITY IN INCREASING ION TRANSPORT BY MUTANT-CFTR AND USES THEREOF

CROSS-REFERENCE TO RELATED APPLICATIONS

This application claims the priority benefit of U.S. provisional application Ser. No. 60/471,060, filed May 16, 2003, which application is incorporated herein by reference in its entirety.

STATEMENT REGARDING FEDERALLY SPONSORED RESEARCH

This invention was made with government support under grant nos. HL73856, EB00415, HL59198, EY13574, and DK35124 awarded by the National Institutes of Health. The government may have certain rights in this invention.

Work on this invention was also supported by grants from the Cystic Fibrosis Foundation and/or from Cystic Fibrosis Foundation Therapeutics.

BACKGROUND OF THE INVENTION

The cystic fibrosis transmembrane conductance regulator protein (CFTR) is a cAMP-activated chloride (Cl$^-$) channel expressed in epithelial cells in mammalian airways, intestine, pancreas and testis. CFTR is the chloride-channel responsible for cAMP-mediated Cl$^{31}$ secretion. Hormones, such as a β-adrenergic agonist, or toxins, such as cholera toxin, lead to an increase in cAMP, activation of cAMP-dependent protein kinase, and phosphorylation of the CFTR Cl$^-$ channel, which causes the channel to open. An increase in the concentration of Ca$^{2+}$ in a cell can also activate different apical membrane channels. Phosphorylation by protein kinase C can either open or shut Cl$^-$channels in the apical membrane. CFTR is predominantly located in epithelia where it provides a pathway for the movement of Cl$^-$ ions across the apical membrane and a key point at which to regulate the rate of transepithelial salt and water transport. CFTR chloride channel function is associated with a wide spectrum of disease, including cystic fibrosis (CF) and with some forms of male infertility, polycystic kidney disease and secretory diarrhea.

The hereditary lethal disease CF is caused by mutations in the gene encoding the CFTR protein, a cAMP-activated Cl$^-$ channel expressed in airway, intestinal, pancreatic, and other secretory and absorptive epithelia. The principal clinical problem in CF is recurrent lung infections resulting in progressive deterioration in lung function. The most common CFTR mutation, deletion of phenylalanine-508 (ΔF508-CFTR), is present in at least one allele in about 90% of CF patients (Egan et al., (2004) *Science* 304:600-602). ΔF508-CFTR causes CL$^-$ impermeability because it is not processed correctly, causing it to be retained at the endoplasmic reticulum (rather than the plasma membrane). ΔF508-CFTR also has reduced intrinsic Cl$^-$ conductance relative to wild type CFTR.

Strategies have been investigated to correct the defects in ΔF508-CFTR cellular processing and intrinsic function in cells. Cell growth at low temperature (<30° C.) (Denning et al., (1992) *Nature* 358, 761-764) or with high concentrations of chemical chaperones such as glycerol (Sato et al., (1996) J. Biol. Chem. 271, 635-638; Brown, et al., (1996) Cell Stress & Chaperones 1, 117-125) corrects partially defective ΔF508-CFTR cellular processing by a mechanism that may involve improved protein folding and stability (Sharma et al., (2001) J. Biol. Chem. 276, 8942-8950). A sustained increase in intracellular calcium concentration by thapsigargin also corrects defective ΔF508-CFTR processing (Egan et al., (2002) Nature Med. 8, 485-492), possibly by interfering with interactions with molecular chaperones.

Compounds like phenylbutyrate facilitate ΔF508-CFTR cellular processing by altering chaperone function and/or transcriptional enhancement (Rubenstein et al., (2000) Am. J. Physiol. 278, C259-C267; Kang et al., (2002) Proc. Natl. Acad. Sci. U.S.A. 99, 838-843). Although these approaches provide insight into mechanisms of ΔF508-CFTR retention at the endoplasmic reticulum, they probably do not offer clinically-useful therapies.

ΔF508-CFTR has significantly impaired channel activity even when present at the cell plasma membrane (Dalemans et al., (1991) Nature 354, 526-528). Cell-attached patch-clamp measurements showed reduced ΔF508-CFTR open channel probability and prolonged closed times even with maximal cAMP stimulation (Haws et al., (1996) Am. J. Physiol. 270, C1544-C1555; Hwang et al., (1997) Am. J. Physiol. 273, C988-C998). Patch-clamp measurements in excised membranes indicated 7-fold reduced ΔF508-CFTR activation after phosphorylation compared to wildtype CFTR. Relatively high concentrations of the flavone genistein (>50 μM, Hwang, et al., (1997) Am. J. Physiol. 273, C988-C998; Wang et al., (2000) J. Physiol. 524, 637-638) or the xanthine isobutylmethylxanthine (>1 mM, Drumm et al., (1991) Science 254, 1797-1799) in combination with cAMP agonists increase ΔF508-CFTR channel activity. Again, these studies have not offered any clinically useful therapies.

There is accordingly still a need for compounds that can activate mutant CFTR, e.g., ΔF508-CTFR, and methods of using such compounds for the study and treatment of CF and the treatment and control of other secretory disorders. The present invention addresses these needs, as well as others.

SUMMARY OF THE INVENTION

The invention provides compositions, including pharmaceutical preparations, which comprise one or more substituted thiophenes (e.g., substituted or unsubstituted cycloalkylthiophenes, including substituted or unsubstituted cycloalkyl[b]thiophenes), benzofuran, pyrimidinetrione, dihydropyridine, tetrahydrocarbazol or anthraquinone compounds. The invention also features methods of use of such compositions in increasing activity of mutant cystic fibrosis transmembrane conductance regulator (CFTR) protein in a cell, e.g., by increasing ion transport in a mutant CFTR.

In one embodiment the invention provides methods of using such compounds to increase ion transport in a mutant CFTR, e.g. ΔF508-CFTR, in a cell by contacting the cell with an effective amount of the compound. In other embodiments, the invention also provides a method of treating a patient suffering from a mutant CFTR, e.g. ΔF508-CFTR, mediated disease or condition, for example CF, by administering to the patient an efficacious amount of a compound of the invention. Kits for use in the subject methods are also provided.

Thus, the present invention provides a method of increasing ion permeability of a cell producing a mutant CFTR protein, particularly a ΔF508-CFTR protein, the method comprising contacting the cell with a compound of the invention in an amount effective to increase ion permeability of the cell, wherein the compound is a substituted thiophene (e.g., substituted or unsubstituted cycloalkylthiophenes, including substituted or unsubstituted cycloalkyl[b]thiophenes) compound, a benzofuran compound, a pyrimidinetrione compound, a dihydropyridine compound, a tetrahydrocarbazol compound, or an anthraquinone compound. In other preferred embodiments, the ion is a chloride ion and the ΔF508-CFTR protein is present at the plasma membrane of said cell.

In one embodiment, the cell contains a recombinant expression cassette that encodes a mutant CFTR, particularly a ΔF508-CFTR protein. In another embodiment, the cell contains a genome that encodes the mutant CFTR protein, e.g., a ΔF508-CFTR protein. In yet another embodiment, the compound of the invention increases the ion transporting activity of said mutant CFTR protein (e.g., ΔF508-CFTR protein). In an embodiment of particular interest, the ion transporting activity increases a rate of transport of ions across the plasma membrane of said cell.

The present invention also provides for a method of treating a subject having a condition associated with a mutant CFTR, particularly a ΔF508-CFTR, where the method comprises administering to the subject an efficacious amount of a compound to increase ion permeability in cells of the subject and thereby treat the condition, wherein the compound is a substituted thiophene (e.g., substituted or unsubstituted cycloalkylthiophenes, including substituted or unsubstituted cycloalkyl[b]thiophenes) compound, a benzofuran compound, a pyrimidinetrione compound, a dihydropyridine compound, a tetrahydrocarbazol compound, or an anthraquinone compound. In a related embodiment, the compound increases the ion transport activity of a mutant CFTR protein, particularly a ΔF508-CFTR, to increase the ion permeability of said cells and the condition is cystic fibrosis.

In one embodiment, the subject, after treatment, has a decrease in mucous or bacterial titer in their lungs, an improvement in pulmonary function, a decrease in coughing or wheezing, an decrease in pancreatic insufficiency, or decrease in electrolyte levels in their sweat. In another embodiment, the subject comprises a gene that encodes a mutant CFTR, e.g., ΔF508-CFTR.

In another embodiment, the method is utilized on a non-human animal. In this embodiment, the compound is generally administered in an amount effective to increase the ion transport activity of a mutant CFTR, e.g., ΔF508-CFTR in the animal. In some embodiments, the animal can be a mammal.

The invention also provides for a pharmaceutical composition comprising a substituted thiophene compound together with at least one of a pharmaceutically acceptable carrier, a pharmaceutically acceptable diluent, a pharmaceutically acceptable excipient and a pharmaceutically acceptable adjuvant. In one embodiment the substituted thiophene is a substituted or unsubstituted tetrahydrocycloalkylthiophene compound. In another embodiment the substituted thiophene compound is a 4,5,6,7tetrahydrobenzo[b]thiophene-3-carboxylic acid amide with an amide linked organic hydrocarbon group of up to 500 Da at the 2 position. In another embodiment, the substituted thiophene compound is a 5,6,7,8-tetrahydro-4H-cyclohepta[b]thiophene-3-carboxylic acid amide with an amide linked organic hydrocarbon group of up to 500 Da at the 2 position. In preferred embodiments, the amide-linked group comprises a substituted or unsubstituted aromatic moiety and the aromatic moiety is substituted by a halide., wherein the tetrahydrocycloalkylthiophene compound is a 4,5,6,7tetrahydrobenzo[b]thiophene-3-carboxylic acid amide with an amide linked organic hydrocarbon group of up to 500 Da at the 2 position. In another embodiment, the compound is a 5,6,7,8-tetrahydro-4H-cyclohepta[b]thiophene-3-carboxylic acid amide with an amide linked organic hydrocarbon group of up to 500 Da at the 2 position. In preferred embodiments, the amide-linked group comprises a substituted or unsubstituted aromatic moiety and the aromatic moiety is substituted by a halide.

In one embodiment of particular interest, the substituted thiophene is a substituted or unsubstituted cycloalkylthiophenes compound having the formula:

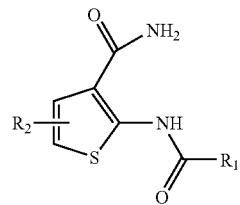

wherein $R_1$ is independently selected from an organic hydrocarbon group of up to 500 Da, and $R_2$ is independently selected from a substituted or unsubstituted cycloalkyl group, such as a substituted or unsubstituted cyclohexyl group, a substituted or unsubstituted cycloheptyl group, and a substituted or unsubstituted anthracenyl group. In one embodiment, the $R_1$ organic hydrocarbon group comprises an aromatic group. In another embodiment, $R_1$, has molecular weight of about 58-165 Da and comprises an aromatic group. In yet another embodiment, the pharmaceutical composition does not contain detectable dimethyl sulfoxide. In an embodiment of particular interest, the substituted thiophene compound has molecular weight of 278-375, a surface area of 296-356 Å$^2$, a polar surface area of 72-98 Å$^2$, 1-3 hydrogen acceptors, and 2 hydrogen donors.

In another embodiment of particular interest the substituted or unsubstituted cycloalkylthiophenes is an unsubstituted cycloalkyl[b]thiophenes having the formula

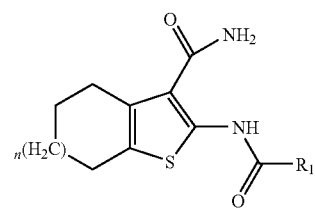

wherein n is 1 or 2, and $R_1$ is an organic hydrocarbon group of up to 500 Da In one embodiment, the organic hydrocarbon group comprises an aromatic group. In another embodiment, $R_1$, has molecular weight of about 58-165 Da and comprises an aromatic group. In yet another embodiment, the pharmaceutical composition does not contain detectable dimethyl sulfoxide. In an embodiment of particular interest, the subject compound has a molecular weight of 278-375, a surface area of 296-356 Å$^2$, a polar surface area of 72-98 Å$^2$, 1-3 hydrogen acceptors, and 2 hydrogen donors.

In one embodiment of particular interest, the substituted thiophene is a substituted or unsubstituted cycloalkylthiophenes compound having the formula:

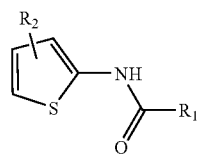

wherein $R_1$ is independently selected form an organic hydrocarbon group of up to 500 Da, and $R_2$ is independently selected form a substituted or unsubstituted cycloalkyl group, such as a substituted or unsubstituted cyclohexyl group, a substituted or unsubstituted cycloheptyl group, and a substituted or unsubstituted anthracenyl group. In one embodiment, the $R_1$ organic hydrocarbon group comprises an aromatic group. In another embodiment, $R_1$, has molecular weight of about 58-165 Da and comprises an aromatic group. In yet another embodiment, the pharmaceutical composition does not contain detectable dimethyl sulfoxide. In an embodiment of particular interest, the subject compound has a molecular weight of 278-375, a surface area of 296-356 Å$^2$, a polar surface area of 72-98 Å$^2$, 1-3 hydrogen acceptors, and 2 hydrogen donors.

The invention also provides for a pharmaceutical composition comprising an activator compound chosen from 1-Furan-2-ylmethyl-5-[1-(4-methoxy-phenyl)-2,5-dimethyl-1H-pyrrol-3-ylmethylene]-pyrimidine-2,4,6-trione, 2-(2-Chloro-benzoylamino)-4,5,6,7-tetrahydro-benzo[b]thiophene-3-carboxylic acid amide. 8-Bromo-6-methyl-2,3,4,9-tetrahydro-carbazol-1-one, 2-Amino-1-(4-tert-butyl-phenoxy)-anthraquinone, 4-(4-Isopropyl-phenyl)-2,6-dimethyl-1,4-dihydro-pyridine-3,5-dicarboxylic acid dimethyl ester, or 3-Benzoylamino-benzofuran-2-carboxylic acid amide. In a preferred embodiment, the pharmaceutical composition does not contain detectable dimethyl sulfoxide. In another preferred embodiment, the pharmaceutical composition further comprises at least one of a pharmaceutically acceptable carrier, a pharmaceutically acceptable diluent, a pharmaceutically acceptable excipient, or a pharmaceutically acceptable adjuvant.

These and other objects and advantages of the invention will be apparent from the detailed description below.

BRIEF DESCRIPTION OF THE DRAWINGS

The invention will be more fully understood by reference to the following drawings, which are for illustrative purposes only.

FIG. 1A. is schematic representation of a high-throughput screening procedure used in the subject methods. Cells co-expressing mutant-CFTR and the halide-sensitive fluorescent protein YFP-H148Q/I152L were grown for 24 h at 27° C. (to give plasma membrane mutant-CFTR expression). After washing, test compounds (2.5 µM) and forskolin (20 µM) were added, and I$^-$ influx was assayed from the time course of YFP-H148Q/I152L fluorescence after adding I$^-$ to the external solution.

FIG. 1B. is a line graph showing representative time courses of YFP-H148Q/I152L fluorescence in control wells (saline, negative control; 50 µM genistein, positive control) with examples of inactive and active test compounds.

FIG. 1C. is a bar graph showing a summary of I$^-$ influx rates (d[I$^-$]/dt) for 100,000 compounds tested in the initial screen.

FIG. 1D. is a line graph showing concentration-response data for selected ΔF508-CFTR-activating or potentiating compounds.

in FIGS. 4A-4C.

FIG. 5A. shows the chemical structure of an extracted minimal consensus substructure and physical property ranges satisfied by >70% of active substituted thiophene.

FIG. 5B. is a line graph showing distribution of calculated AlogP for the active substituted thiophene is a statistically distinct subpopulation of all substituted thiophenes in the library (Mann-Whitney, $p<10^{-5}$).

FIG. 5C. is a line graph showing the results of cross-validation studies. The poorest performing model clearly differentiated active and inactive substituted thiophenes in the test set and for all substituted thiophenes in the study (Mann-Whitney, $p<10^{-5}$) (see text for explanations). The AUC of Receiver-Operator Curves (ROC, in grey) for the test set and all substituted thiophenes are 0.98 and 0.99, respectively.

FIG. 5D. shows chemical structures of favorable and unfavorable structural elements identified by the Bayesian learning model.

FIG. 5E. shows examples of a structure-activity series derived from the screening data.

FIG. 6. shows chemical structures of exemplary substituted thiophene compounds, and preliminary data as to their activity as mutant-CFTR protein activators or potentiators. The ID, structure, formula, molecular weight, cluster, cluster span, logp, logd, logsw, Vmax, Kd and the effect of the compounds on mutant-CFTR function is shown. Compounds are classified as either "good", "moderate" or "inactive", based on their-effect on mutant-CFTR function, as indicated by the preliminary data.

Figure 2A:
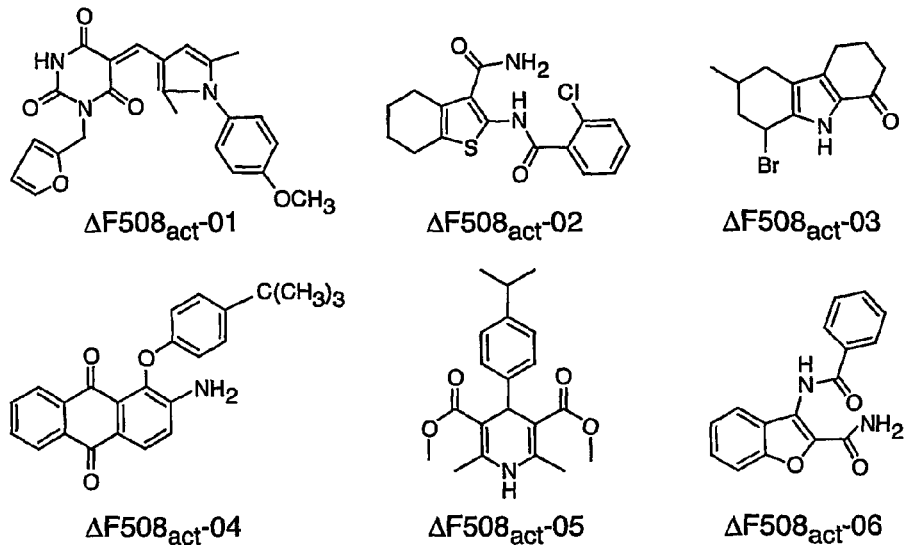
FIG. 2A. shows chemical structures of the compounds of each chemical class having the most potency in increasing ion transport of the mutant CFTR ΔF508.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It should be noted that, as used herein and in the appended claims, the singular forms "a", "and", and "the" include plural referents unless the context clearly dictates otherwise. Thus, for example, reference to "a compound" includes a plurality of such compounds, and reference to "the cell" includes reference to one or more cells and equivalents thereof known to those skilled in the art, and so forth.

The publications discussed herein are provided solely for their disclosure prior to the filing date of the present application, and are incorporated herein by reference. Nothing herein is to be construed as an admission that the present invention is not entitled to antedate such publication by virtue of prior invention. Further, the dates of publication provided may be different from the actual publication dates that may need to be independently confirmed.

The definitions used herein are provided for reason of clarity, and should not be considered as limiting. The technical and scientific terms used herein are intended to have the same meaning as commonly understood by those of ordinary skill in the art to which the invention pertains.

DETAILED DESCRIPTION OF THE INVENTION

The invention provides compositions, pharmaceutical preparations and methods for activation of mutant-cystic fibrosis transmembrane conductance regulator protein (mutant-CFTR) that are useful for the study and treatment of cystic fibrosis (CF).

In one embodiment, the compositions and pharmaceutical preparations of the invention may comprise one or more compounds disclosed herein, which compounds can be a substituted thiophene, benzofuran, pyrimidinetrione, dihydropyridine, tetrahydrocarbazols or anthraquinone compound. The compositions and pharmaceutical preparations of the invention may additionally comprise one or more pharmaceutically acceptable carriers, excipients and/or adjuvants.

The invention provides methods increasing ion transport in a mutant-CFTR, e.g., ΔF508-CFTR, in a cell by contacting the cell with an effective amount of one or more of the compounds set forth above. In other embodiments, the invention also provides a method of treating a patient suffering from a mutant-CFTR-mediated disease or condition, for example CF, by administering to the patient an efficacious amount of one or more of the compounds set forth above. Kits for use in the subject methods are also provided.

In one aspect of particular interest, the invention is based on the discovery of a genus of substituted thiophene compounds that are high-affinity ΔF508-CFTR activators or potentitators.

In one aspect of particular interest, the invention is based on the discovery of genera of benzofuran, pyrimidinetrione, dihydropyridine, tetrahydrocarbazols or anthraquinone compounds which have activity as potentiators or activators of ΔF508-CFTR protein.

In describing invention, the structure of the compounds of the invention will be described first. Then, pharmaceutical formulations containing the compounds will be discussed, followed by a description of their methods of use.

DEFINITIONS

A "mutant cystic fibrosis transmembrane conductance regulator protein", or "mutant-CFTR" is the protein that results from a mutation, e.g., deletion mutation, insertion mutation, or point (substitution) mutation of the CFTR gene product. As used herein a "mutant cystic fibrosis transmembrane conductance regulator protein", or "mutant-CFTR" resulting from a mutation compared to a functional (e.g., wildtype) CFTR encompasses the following dysfunctions associated with the mutation: (i) aberrant CFTR production (e.g., at the level of transcription or translation); (ii) aberrant folding and/or trafficking; (iii) abnormal regulation of conductance; (iv) decreases in chloride conductance; (v) reduction in synthesis; and the like. A "mutant-CFTR gene" is a gene, or coding sequence, which encodes a mutant-CFTR. For the purposes of this application, the terms "genome" and "gene" are used interchangeably, e.g. "genome that encodes mutant-CFTR" and "gene that encodes mutant-CFTR".

A "mutant-CFTR protein-mediated condition" means any condition, disorder or disease, or symptom of such condition, disorder, or disease, that results from or is correlated to the presence of a mutant-CFTR, e.g., ΔF508-CFTR, e.g., chloride ion impermeability caused by reduced activity of ΔF508-CFTR in ion transport relative to a wild-type CFTR. A "mutant-CFTR protein-mediated condition" encompasses conditions in an affected subject which are associated with the presence of a ΔF508-CFTR mutation on at least one allele, thus including subjects that carry a ΔF508-CFTR mutation on both alleles as well as compound heterozygous subjects having two different mutant forms of CFTR, e.g., a subject with one copy of ΔF508-CFTR and a copy of different mutant form of CFTR.

Such conditions, disorders, diseases, or symptoms thereof are treatable by specific activation of mutant-CFTR activity, e.g., activation of mutant-CFTR ion transport. ΔF508-CFTR is correlated to the presence of cystic fibrosis (CF), and a description of this disease, including its symptoms, is found in Accession No. 602421 (entitled cystic fibrosis transmembrane conductance regulator; CFTR), and Accession No. 219700 (entitled Cystic fibrosis; CF) of the Online Mendelian Inheritance of Man database, as found at the world wide website of the National Institute of Health at ncbi.nlm.nih.gov. Symptoms of mutant-CFTR protein-mediated conditions include meconium ileus, liver disease including biliary tract obstruction and stenosis, pancreatic insufficiency, pulmonary disease including chronic Pseudomonas aeruginosa infections and other infections of the lung, infertility associated with abnormal vas deferens development or abnormal cervical mucus, and carcinoma including adenocarcinoma. Many subjects that have a mutant-CFTR protein-mediated condition are homozygous for a gene encoding a ΔF508-CFTR protein.

A "ΔF508-cystic fibrosis transmembrane conductance regulator protein", or "ΔF508-CFTR" is the protein that results from the deletion of a phenylalanine residue at amino acid position 508 of the CFTR gene product. A "ΔF508-

CFTR gene" is a gene, or coding sequence, which encodes ΔF508-CFTR. A ΔF508-CFTR gene usually results from deletion of three nucleotides corresponding to the phenylalanine residue at amino acid position 508 of the encoded CFTR gene product. For the purposes of this application, the terms "genome" and "gene" are used interchangeably, e.g. "genome that encodes ΔF508-CFTR" and "gene that encodes ΔF508-CFTR". For an example of a gene that encodes ΔF508-CFTR, see, e.g. WO 91/02796.

A "mutant-CFTR activator" as used herein is a compound that increases the level of ion transport by a mutant-CFTR relative to ion transport in the absence of the compound, and particularly with respect to transport of chloride ions. CFTR activators of the invention of particular interest are those that are specific mutant-CFTR activators, e.g., compounds that activate mutant-CFTR activity rather than affecting CFTR cellular misprocessing. Mutant-CFTR activators are usually high-affinity mutant-CFTR activators, e.g., have an affinity for mutant-CFTR of at least about one micromolar, about one to five micromolar, about 200 nanomolar to one micromolar, about 50 nanomolar to 200 nanomolar, or below 50 nanomolar.

A "ΔF508-CFTR activator" as used herein is a compound that increases the level of ion transport by ΔF508-CFTR relative to ion transport in the absence of the compound, and particularly with respect to transport of chloride ions. CFTR activators of the invention of particular interest are those that are specific ΔF508-CFTR activators, e.g., compounds that activate ΔF508-CFTR activity rather than affecting CFTR cellular misprocessing. ΔF508-CFTR activators are usually high-affinity ΔF508-CFTR activators, e.g., have an affinity for ΔF508-CFTR of at least about one micromolar, about one to five micromolar, about 200 nanomolar to one micromolar, about 50 nanomolar to 200 nanomolar, or below 50 nanomolar.

As used herein and in the cystic fibrosis field a "potentiator" refers to a compound that increases a basal level of ion transport by a mutant-CFTR (e.g,. ΔF508CFTR), where the mutant CFTR (in the absence of the compound) exhibits aberrantly low levels of ion transport relative to wildtype CFTR. As such, a "mutant-ΔF508 CFTR potentiator" refers to a potentiator compound that, provides for increased level of ion transport by a mutant-ΔF508 CFTR relative to ion transport capability of the mutant-CFTR in the absence of the compounds.

"In combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

The term "isolated compound" means a compound which has been substantially separated from, or enriched relative to, other compounds with which it occurs in nature. Isolated compounds are usually at least about 80%, more usually at least 90% pure, even more preferably at least 98% pure, most preferably at least about 99% pure, by weight. The present invention is meant to comprehend diastereomers as well as their racemic and resolved, enantiomerically pure forms and pharmaceutically acceptable salts thereof "Treating" or "treatment" of a condition or disease includes: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

A "therapeutically effective amount" or "efficacious amount" means the amount of a compound that, when administered to a mammal or other subject for treating a disease, is sufficient to effect such treatment for the disease. The "therapeutically effective amount" will vary depending on the compound, the disease and its severity and the age, weight, etc., of the subject to be treated.

The terms "subject" and "patient" mean a member or members of any mammalian or non-mammalian species that may have a need for the pharmaceutical methods, compositions and treatments described herein. Subjects and patients thus include, without limitation, primate (including humans), canine, feline, ungulate (e.g., equine, bovine, swine (e.g., pig)), avian, and other subjects. Humans and non-human animals having commercial importance (e.g., livestock and domesticated-animals) are of particular interest.

"Mammal" means a member or members of any mammalian species, and includes, by way of example, canines; felines; equines; bovines; ovines; rodentia, etc. and primates, particularly humans. Non-human animal models, particularly mammals, e.g. primate, murine, lagomorpha, etc. may be used for experimental investigations.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound (e.g., substituted thiophene) compound employed and the effect to be achieved, and the pharmacodynamics associated with each compound in the host.

The term "physiological conditions" is meant to encompass those conditions compatible with living cells, e.g., predominantly aqueous conditions of a temperature, pH, salinity, etc. that are compatible with living cells.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, dileuent, carrier and adjuvant" as used in the specification and claims includes both one and more than one such excipient, dileuent, carrier, and adjuvant.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like. In some embodiments the composition is suitable for administration by a tansdermal route, using a penetration enhancer other than DMSO. In other embodiments, the pharmaceutical compositions are suitable for administration by a route other than transdermal administration.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an aLkali metal ion, an alkaline earth ion, or an aluminum ion; or coordinates with an organic base such as ethanolamine, diethanolamine, triethanolamine, tromethamine, N-methylglucamine, and the like.

A "pharmaceutically acceptable ester" of a compound of the invention means an ester that is pharmaceutically acceptable and that possesses the desired pharmacological activity of the parent compound, and includes, but is not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

A "pharmaceutically acceptable enol ether" of a compound of the invention means an enol ether that is pharmaceutically acceptable and that possesses the desired pharmacological activity of the parent compound, and includes, but is not limited to, derivatives of formula C=C(OR) where R is hydrogen, alkyl, alkenyl, alkynyl,-aryl; heteroaryl, aralkyl, heteroaralkyl, cycloalkyl or heterocyclyl.

A "pharmaceutically acceptable enol ester" of a compound of the invention means an enol ester that is pharmaceutically acceptable and that possesses the desired pharmacological activity of the parent compound, and includes, but is not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl.

A "pharmaceutically acceptable solvate or hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

"Pro-drugs" means any compound that releases an active parent drug according to formula (I) in vivo when such prodrug is administered to a mammalian subject. Prodrugs of a compound of formula (I) are prepared by modifying functional groups present in the compound of formula (I) in such a way that the modifications may be cleaved in vivo to release the parent compound. Prodrugs include compounds of formula (I) wherein a hydroxy, amino, or sulfhydryl group in compound (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of formula (I), and the like.

The term "organic group" and "organic radical" as used herein means any carbon-containing group, including hydrocarbon groups that are classified as an aliphatic group, cyclic group, aromatic group, functionalized derivatives thereof and/or various combination thereof. The term "aliphatic group" means a saturated or unsaturated linear or branched hydrocarbon group and encompasses alkyl, alkenyl, and alkynyl groups, for example. The term "alkyl group" means a substituted or unsubstituted, saturated linear or branched hydrocarbon group or chain (e.g., $C_1$ to $C_8$ ) including, for example, methyl, ethyl, isopropyl, tert-butyl, heptyl, iso-propyl, n-octyl, dodecyl, octadecyl, amyl, 2-ethylhexyl, and the like. Suitable substituents include carboxy, protected carboxy, amino, protected amino, halo, hydroxy, protected hydroxy, nitro, cyano, monosubstituted amino, protected monosubstituted amino, disubstituted amino, $C_1$ to $C_7$ alkoxy, $C_1$ to $C_7$ acyl, $C_1$ to $C_7$ acyloxy, and the like.

The term "substituted alkyl" means the above defined alkyl group substituted from one to three times by a hydroxy, protected hydroxy, amino, protected amino, cyano, halo, trifloromethyl, mono-substituted amino, di-substituted amino, lower alkoxy, lower alkylthio, carboxy, protected carboxy, or a carboxy, amino, and/or hydroxy salt. As used in conjunction with the substituents for the heteroaryl rings, the terms "substituted (cycloalkyl)alkyl" and "substituted cycloalkyl" are as defined below substituted with the same groups as listed for a "substituted alkyl" group. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group, and may include one or more heteroatoms, and which are further defined below. The term "heterocyclic group" means a closed ring hydrocarbon in which one or more of the atoms in the ring are an element other than carbon (e.g., nitrogen, oxygen, sulfur, etc.), and are further defined below.

"Organic groups" may be functionalized or otherwise comprise additional functionalities associated with the organic group, such as carboxyl, amino, hydroxyl, and the like, which may be protected or unprotected. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ethers, esters, haloalkyls, nitroalkyls, carboxyalkyls, hydroxyalkyls, sulfoalkyls, etc.

The terms "halo" and "halogen" refer to the fluoro, chloro, bromo or iodo groups. There can be one or more halogen, which are the same or different. Halogens of particular interest include chloro and bromo groups.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" means a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted for one of the above cycloalkyl rings. Examples of such a group include (cyclohexyl)methyl, 3-(cyclopropyl)-n-propyl, 5-(cyclopentyl)hexyl, 6-(adamantyl) hexyl, and the like.

The term "substituted phenyl" specifies a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N-($C_1$ to $C_6$ alkyl)carboxamide, protected N-($C_1$ to $C_6$ alkyl) carboxamide, N,N-di($C_1$ to $C_6$ alkyl)carboxamide, trifluoromethyl, N-(($C_1$ to $C_6$ alkyl)sulfonyl)amino, N-(phenylsulfonyl)amino or phenyl, substituted or unsubstituted, such that, for example, a biphenyl or naphthyl group results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(isopropyl)phenyl, 2, 3, or 4-ethylphenyl, 2, 3 or 4-(n-propyl) phenyl and the like; a mono or di(alkoxy)phenyl group, for example, 2,6-dimethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(amiomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The term "(substituted phenyl)alkyl" means one of the above substituted phenyl groups attached to one of the above-described alkyl groups. Examples of include such groups as 2-phenyl-1-chloroethyl, 2-(4'-methoxyphenyl)ethyl, 4-(2',6'-dihydroxy phenyl)n-hexyl, 2-(5'-cyano-3'-methoxyphenyl) n-pentyl, 3-(2',6'-dimethylphenyl)n-propyl, 4-chloro-3-aminobenzyl, 6-(4'-methoxyphenyl)-3-carboxy(n-hexyl), 5-(4'-aminomethylphenyl)-3-(aminomethyl)n-pentyl, 5-phenyl-3-oxo-n-pent-1-yl, (4-hydroxynapth-2-yl)methyl and the like.

As noted above, the term "aromatic" or "aryl" refers to six membered carbocyclic rings. Also as noted above, the term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms.

Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl,.thiadiazolyl, oxadiazolyl, tetrazolyl, thiatriazolyl, oxatriazolyl, pyridyl, pyrimidyl, pyrazinyl,.pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The term "(monosubstituted)amino" refers to an amino group with one substituent chosen from the group consisting of phenyl, substituted phenyl, alkyl, substituted alkyl, $C_1$ to $C_4$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" denotes an alkyl group as defined above, substituted at any position by a heteroaryl group, as above defined.

"Optional" or "optionally" means that the subsequently described event, circumstance, feature or element may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R— and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof A mixture containing equal proportions of the enantiomers is called a "racemic mixture."

The compounds of this invention may possess one or more asymmetric centers; such compounds can therefore be produced as individual (R)— or (S)— stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

Overview

The invention provides compounds that act as activators or potentiators of mutant cystic fibrosis transmembrane conductance regulator protein, e.g., ΔF508-CFTR, (generally referred to herein as "activator compounds", "activators", "potentiator compounds", or "potentiators") and methods of their use in high affinity activation, and for the study and treatment of, mutant-CFTR-mediated diseases and conditions. Specifically, the invention provides high-affinity small-molecule compounds that act as activators or potentiators of mutant-CFTR, e.g., ΔF508-CFTR, Cl$^-$ conductance. The compounds contemplated by the invention include those of the following structural classes: (1) substituted thiophenes (e.g., substituted or unsubstituted cycloalkylthiophenes, including substituted or unsubstituted cycloalkyl[b]thiophenes); (2) benzofurans; (3) pyrimidinetriones; (4) dihydropyridines, (5) tetrahydrocarbazols or (6) anthraquinones. Substituted thiophene compounds are of particular interest, particularly substituted or unsubstituted cycloalkylthiophenes, more particularly substituted or unsubstituted cycloalkyl[b]thiophenes.

A collection of 100,000 chemically-diverse compounds were screened using a sensitive cell-based assay to detect mutant-CFTR mediated halide influx. The clonal epithelial cell line used for screening was generated by co-transfection of FRT cells with cDNAs encoding ΔF508-CFTR and a YFP mutant (H148Q/152L) developed previously whose fluorescence is highly sensitive to iodide (50% fluorescence quenching at 2 mM I$^-$). Incubation of ΔF508-CFTR/YFP-transfected cells for 24 hours at 27° C. produced consistent strong ΔF508-CFTR expression at the cell surface as needed for screening of rapidly-acting potentiators of ΔF508-CFTR function. More than 30 mutant-CFTR potentiator compounds were identified by the initial cell-based fluorescence screen with apparent submicromolar activating potencies. Electrophysiological analysis confirmed strong ΔF508-CFTR activating potency for most of the compounds. The most potent compounds inducing ΔF508-CFTR-mediated Cl$^-$ currents were optimized by screening of structural analogs. In particular, several substituted thiophenes were identified that activated ΔF508-CFTR Cl$^-$ conductance reversibly with $K_d$ down to 60 nM.

Secondary analysis of the mutant-CFTR potentiators indicated that they did not induce Cl$^-$ currents in the absence of CFTR, and that Cl$^-$ currents in ΔF508-CFTR-expressing cells required cAMP and were inhibited by the thiazolidinone CFTR$_{inh}$-172. The potentiators were rapidly-acting, reversible and non-toxic. Whole-cell patch-clamp experiments showed that the activated currents were as expected for CFTR currents, but not other types of epithelial Cl$^-$ channels; The potentiators did not elevate cellular cAMP, nor did they inhibit cellular phosphatase activity. Interestingly, the ΔF508-CFTR potentiators also activated wildtype CFTR, but did so with different relative-potencies than for activation of ΔF508-CFTR. None of the compounds activated G551D-CFTR mutant even in the presence of high concentrations of cAMP agonists, nor did they cause ER-to-plasma membrane transport of ΔF508-CFTR as assessed functionally and biochemically.

Analysis of the physical and structural determinants of the substituted thiophene class of mutant-CFTR potentiators using Bayesian methods revealed that they represent a statistically distinct subset of all substituted thiophenes in the screening library. The learned model effectively predicted activities of substituted thiophenes in cross-validation experiments. In an initial test of the general validity of this model, a series of about 135 previously untested substituted thiophenes were selected from a commercial source using simple similarity comparisons. The Bayesian model correctly predicted the activities of 3 of the 3 most active compounds and the inactivity of about 90% of the inactive compounds.

As such, high-affinity mutant-CFTR potentiators with novel chemical structures are provided. Without wishing to be bound by this theory, it is speculated that the compounds probably activate the ΔF508-CFTR by a direct binding mechanism, most likely to a site on the first nucleotide binding domain of CFTR where the ΔF508 mutation site is located.

The compositions and methods of the invention will now be described in more detail.

Compositions

Substituted Thiophene Compounds

The substituted thiophene compounds used in the compositions and methods of the invention comprise a structure with the following features: a) a 4,5-, or 3,4-fused cycloalkythiophene with the fused ring of the cycloalkylthiophene being a 6 or 7-membered aliphatic ring, an aromatic ring, or an anthracenyl ring, b) an $R_1$ group at the 2 position, which may be attached via a linker such as an amide-linker, and optionally c) a hydrogen donor such as an unsubstituted carboxamide in the 3-position. In certain embodiments, the substituted thiophene compounds used in the present invention are unsubstituted cycloalkyl[b]thiophene-3-carboxylic acid amides that contain an amide-linked variable $R_1$ group at the 2 position.

In one embodiment, the substituted thiophene is a substituted or unsubstituted cycloalkylthiophenes compound having the formula:

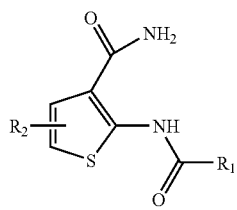

wherein $R_1$ is independently selected form an organic group that has a molecular weight of up to about 500 Da, about 35 to about 300 Da, about 40 to about 190 Da, or, in certain embodiments, a molecular weight of about 68-about 165 Da, and $R_2$ is independently selected form a substituted or unsubstituted cycloalkyl group, such as a substituted or unsubstituted cyclohexyl group, a substituted or unsubstituted cycloheptyl group, and a substituted or unsubstituted anthracenyl group. The $R_1$ organic group may have an N atom instead of a C atom at 1, 2, 3, or 4 positions, and may comprise a substituted or substituted aromatic hydrocarbon ring. $R_1$ cannot be a hydrogen atom, and usually contains up to about 30 (i.e. up to about 25, up to about 20, up to about 15, up to about 10, up to about 5) carbon atoms. In one embodiment, the $R_1$ organic hydrocarbon group comprises an aromatic group. In another embodiment, $R_1$, has molecular weight of about 58-165 Da and comprises an aromatic group. In an embodiment of particular interest, the tetrahydrocycloalkylthiophene compound has molecular weight of 278-375, a surface area of 296-356 $Å^2$, a polar surface area of 72-98 $Å^2$, 1-3 hydrogen acceptors, and 2 hydrogen donors.

In another embodiment the substituted or unsubstituted cycloalkylthiophenes is an unsubstituted cycloalkyl[b] thiophenes having the formula

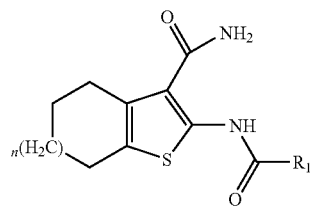

wherein n is 1 or 2, $R_1$ is independently selected form an organic group that has a molecular weight of up to about 500 Da, about 35 to about 300 Da, about 40 to about 190 Da, or, in certain embodiments, a molecular weight of about 68-about 165 Da. The $R_1$ organic group may have an N atom instead of a C atom at 1, 2, 3, or 4 positions, and may comprise a substituted or substituted aromatic hydrocarbon ring. $R_1$ cannot be a hydrogen atom, and usually contains up to about 30 (i.e. up to about 25, up to about 20, up to about 15, up to about 10, up to about 5) carbon atoms. In one embodiment, the organic hydrocarbon group comprises an aromatic group. In another embodiment, $R_1$, has molecular weight of about 58-165 Da and comprises an aromatic group. In an embodiment of particular interest, the subject compound has a molecular weight of 278-375, a surface area of 296-356 $Å^2$, a polar surface area of 72-98 $Å^2$, 1-3 hydrogen acceptors, and 2 hydrogen donors.

In another embodiment, the substituted thiophene is a substituted or unsubstituted cycloalkylthiophenes compound having the formula:

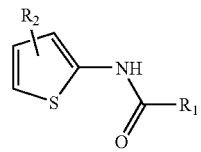

wherein $R_1$ is independently selected form an organic group that has a molecular weight of up to about 500 Da, about 35 to about 300 Da, about 40 to about 190 Da, or, in certain embodiments, a molecular weight of about 68-about 165 Da, and $R_2$ is independently selected form a substituted or unsubstituted cycloalkyl group, such as a substituted or unsubstituted cyclohexyl group, a substituted or unsubstituted cycloheptyl group, and a substituted or unsubstituted anthracenyl group. The $R_1$ organic group may have an N atom instead of a C atom at 1, 2, 3, or 4 positions, and may comprise a substituted or substituted aromatic It will also be appreciated by those skilled in the art, although such protected derivatives of compounds of formula (I), as described above, may not possess pharmacological activity as such, they may be administered to a mammal and thereafter metabolized in the body to form compounds of the invention which are pharmacologically active. Such derivatives may therefore be described as "prodrugs". All prodrugs of compounds of formula (I) are included within the scope of the invention.

The following Reaction Scheme illustrate methods to make the substituted thiophene compounds of the invention. It is understood that one of ordinary skill in the art would be able to make the compounds of the invention by similar methods or by methods known to one skilled in the art. In general, starting components may be obtained from sources such as Aldrich, or synthesized according to sources known to those of ordinary skill in the art (see, e.g., Smith and March, *March's Advanced Organic Chemistry: Reactions, Mechanisms, and Structure,* 5th edition (Wiley Interscience, New York)). Moreover, the various substituted group $R_1$ of the substituted thiophene compounds of the invention may be attached to the starting components, intermediate components, and/or final products according to methods known to those of ordinary skill in the art.

The following Reaction Scheme is directed to the preparation of compounds of formula (1), which are compounds of the invention as described above where $R_1$ is as described above.

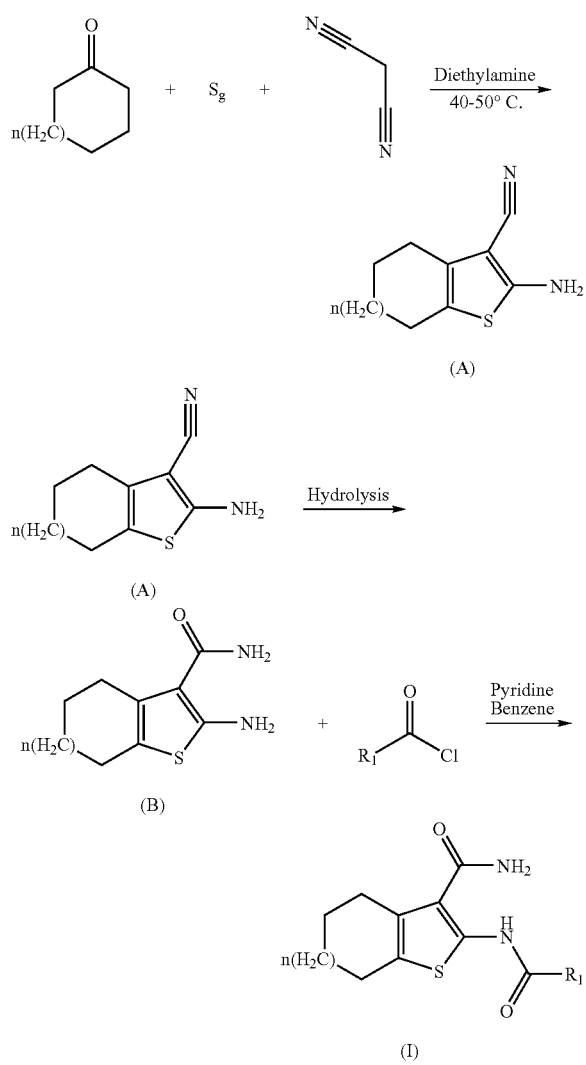

In general, compounds of Formula (I) are prepared by first combining cyclohexanone and sulfur with 2-cyanoacetamide in the presence of diethylamnine at 40-50° C. to yield the compound of formula (A). The compound of formula (A) is then subjected to hyrdrolysis to hydrocarbon ring. $R_1$ cannot be a hydrogen atom, and usually contains up to about 30 (i.e. up to about 25, up to about 20, up to about 15, up to about 10, up to about 5) carbon atoms. In one embodiment, the $R_1$ organic hydrocarbon group comprises an aromatic group. In another embodiment, $R_1$ has molecular weight of about 58-165 Da and comprises an aromatic group. In an embodiment of particular interest, the subject compound has a molecular weight of 278-375, a surface area of 296-356 Å$^2$, a polar surface area of 72-98 Å$^2$, 1-3 hydrogen acceptors, and 2 hydrogen donors.

In one embodiment, the molecular weight of the subject compounds lies in the range of 230-600 Da, usually in the range of 250 to 400 Da, and, in many embodiments, the active compounds (i.e., active compounds having an AlogP of 2.31-3.59) have molecular weight of 278-375, a surface area of 296-356 Å$^2$, a polar surface area of 72-98 Å$^2$, 1-3 hydrogen acceptors, and 2 hydrogen donors.

In some embodiments, the $R_1$ group of the substituted thiophene compounds may be an alkyl group (i.e., comprising a saturated or unsaturated, straight, branched, cyclic, or polycyclic, aliphatic hydrocarbon moiety that may be substituted at any position), any aryl group, (i.e., comprising a monovalent, aromatic, hydrocarbon, ring system that may be substituted at any position), or a combination thereof (an aralkyl group), and the like.

In certain embodiments, $R_1$ is a substituted (e.g. substituted with a halide or $C_1$-$C_6$ alkyl group, etc.) or unsubstituted benzyl group that may have an amino group for linkage to the core structure. In other embodiments, $R_1$ contains a substituted or unsubstituted straight or cyclical aliphatic hydrocarbon group containing up to 8 (e.g., 5, 6, 7, or 8) hydrocarbons. Representative examples from each of these classes of $R_1$ groups for mutant-CFTR-activating substituted thiophene compounds have the following formula:

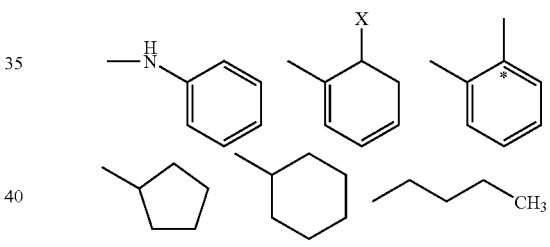

where "*" is a multicenter attachment, and X is any halide.

As such, representative substituted thiophene compounds that activate mutant-CFTR include the following: 2-Benzoylamino-4,5,6,7-tetrahydro-benzo[b]thiophene-3-carboxylic acid amide; 2-(2,3,4,or 5-halo-benzoylamino)-4,5,6,7-tetrahydro-benzo[b]thiophene-3 carboxylic acid amide; 2-(2,3,4,or 5-methyl or ethyl-benzoylamino)-4,5,6,7-tetrahydro-benzo[b]thiophene-3-carboxylic acid amide; 2-(Cyclopentanecarbonyl-amino)-4,5,6,7-tetrahydro-benzo[b]thiophene-3-carboxylic acid amide; 2-(Cyclohexanecarbonyl-amino)-4,5,6,7-tetrahydro-benzo[b]thiophene-3-carboxylic acid amide; and 2-Hexanoylamino-4,5,6,7-tetrahydro-benzo[b]thiophene-3-carboxylic acid amide.

Further exemplary mutant-CFTR activating substituted thiophene compounds that are shown in FIG. 6, as well as examples of compounds related but different to the above substituted thiophene compounds that do not activate mutant-CFTR. FIG. 6 also includes data as to the activity of these compounds with respect to mutant-CFTR ion transport.

Synthesis of Substituted Thiophene Compounds

Substituted thiophene compounds of the invention may be prepared according to methods known to one skilled in the art, or by methods similar to the method described below.

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein.

The use of protecting groups is described in detail in Theodora W. Greene, Peter G. M. Wuts, *Protective Groups in Organic Synthesis* (1999), 3rd Ed., Wiley-Interscience. The protecting group may also be a polymer resin such as a Wang resin or a 2-chlorotrityl chloride resin. yield the compound of formula (B). The compound of formula (B) in pyridine is then reacted with the $R_1$ group containing 2-chlorobenzoyl-chloride in benzene and recrystalized in ethyl acetate-hexane to yield the desired product of Formula (I).

Structures were confirmed by $^1$H-NMR and Mass spectrometry.

Compounds of Other Structural Classes

In addition to the substituted thiophene compounds, compounds of five different structural classes were identified as having activity in promoting ΔF508CFTR ion transport. These include benzofurans, pyrimidinetriones, dihydropyridines, tetralydrocarbazols and anthraquinones. The structures of compounds exemplary of each of these five structural classes are shown in FIG. 2A.

Pharmaceutical Preparations Containing Compounds of the Invention

Also provided by the invention are pharmaceutical preparations of the subject compounds described above. The subject compounds can be incorporated into a variety of formulations for therapeutic administration by a variety of routes. More particularly, the compounds of the present invention can be formulated into pharmaceutical compositions by combination with appropriate, pharmaceutically acceptable carriers, diluents, excipients and/or adjuvants, and may be formulated into preparations in solid, semi-solid, liquid or gaseous forms, such as tablets, capsules, powders, granules, ointments, solutions, suppositories, injections, inhalants and aerosols. In most embodiments, the formulations are free of detectable DMSO (dimethyl sulfoxide), which is not a pharmaceutically acceptable carrier, diluent, excipient, or adjuvant, particularly in the context of routes of administration other than transdermal routes. Where the formulation is for transdermal administration, the compounds are preferably formulated either without detectable DMSO or with a carrier in addition to DMSO. The formulations may be designed for administration to subjects or patients in need thereof via a number of different routes, including oral, buccal, rectal, parenteral, intraperitoneal, intradermal, intratracheal, etc., administration.

Pharmaceutically acceptable excipients usable with the invention, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985; Remington: The Science and Practice of Pharmacy, A. R. Gennaro, (2000) Lippincott, Williams & Wilkins. The composition or formulation to be administered will, in any event, contain a quantity of the agent adequate to achieve the desired state in the subject being treated.

Dosage Forms of Compounds of the Invention

In pharmaceutical dosage forms, the subject compounds of the invention may be administered in the form of their pharmaceutically acceptable salts, or they may also be used alone or in appropriate association, as well as in combination, with other pharmaceutically active compounds. The following methods and excipients are merely exemplary and are in no way limiting.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes, such as intrapulmonary or intranasal delivery.

Conventional and pharmaceutically acceptable routes of administration include intranasal, intrapulmonary intramuscular, intratracheal, intratumoral, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

In one embodiment of particular interest, the compounds of the invention are administered in aerosol formulation via intrapulmonary inhalation. The compounds of the present invention can be formulated into pressurized acceptable propellants such as dichlorodifluoromethane, propane, nitrogen and the like.

Mechanical devices designed for intrapulmonary delivery of therapeutic products, include but are not limited to nebulizers, metered dose inhalers, and powder inhalers, all of which are familiar to those of skill in the art. Specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; the Spinhaler powder inhaler, manufactured by Fisons Corp., Bedford, Mass.; the "standing cloud" device of Inhale Therapeutic Systems, Inc., San Carlos, Calif.; the AIR inhaler manufactured by Alkennes, Cambridge, Mass.; and the AERx pulmonary drug delivery system manufactured by Aradigm Corporation, Hayward, Calif. Of particular interest are the PARI LC PLUS®, the PARI LC STAR®, and the PARI BABY™ nebulizers by PARI Respiratory Equipment, Inc., Monterey, Calif.

Formulations for use with a metered dose inhaler device will generally comprise a finely divided powder. This powder may be produced bylyophilizing and then milling a liquid conjugate formulation and may also contain a stabilizer such as human serum albumin (HSA). Typically, more than 0.5% (w/w) HSA is added. Additionally, one or more sugars or sugar alcohols may be added to the preparation if necessary. Examples include lactose maltose, mannitol, sorbitol, sorbitose, trehalose, xylitol, and xylose. The amount added to the formulation can range from about 0.01 to 200% (w/w), preferably from approximately 1 to 50%, of the conjugate present. Such formulations may then lyophilized and milled to the desired particle size.

The properly sized particles may then suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants may include sorbitan trioleate and soya lecithin. Oleic acid may also be useful as a surfactant. This mixture may then loaded into the delivery device. An example of a commercially available metered dose inhaler suitable for use in the present invention is the Ventolin metered dose inhaler, manufactured by Glaxo Inc., Research Triangle Park, N.C.

Formulations for powder inhalers may comprise a finely divided dry powder containing conjugate and may also include a bulking agent, such as lactose, sorbitol, sucrose, or mannitol in amounts which facilitate dispersal of the powder from the device, e.g., 50% to 90% by weight of the formulation. The particles of the powder may have aerodynamic properties in the lung corresponding to particles with a density of about 1 g/cm.sup.2 having a median diameter less than 10 micrometers, preferably between 0.5 and 5 micrometers, most preferably of between 1.5 and 3.5 micrometers. An example of a powder inhaler suitable for use in accordance with the teachings herein is the Spinhaler powder inhaler, manufactured by Fisons Corp., Bedford, Mass. The powders for these devices may be generated and/or delivered by methods disclosed in U.S. Pat. Nos. 5,997,848, 5,993,783, 5,985,248, 5,976574, 5,922,354, 5,785,049 and 5,654,007.

For oral preparations, the subject compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

The subject compounds of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agent can also be delivered to the subject by enteral administration. Enteral routes of administration include, but are not necessarily limited to, oral and rectal (e.g., using a suppository) delivery.

Furthermore, the subject compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Dosages of the Compounds of the Invention

Depending on the subject and condition being treated and on the administration route, the subject compounds may be administered in dosages of, for example, 0.1 µg to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be about ten times the injection dose. Higher doses may be used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Although the dosage used will vary depending on the clinical goals to be achieved, a suitable dosage range is one which provides up to about 1 µg to about 1,000 µg or about 10,000 µg of subject composition to reduce a symptom in a subject animal.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the invention. Similarly, unit dosage forms for injection or intravenous administration may comprise the compound (s) in a composition as a solution in sterile water, normal saline or another pharmaceutically acceptable carrier.

Combination Therapy Using the Compounds of the Invention

For use in the subject methods, the subject compounds may be formulated with or otherwise administered in combination with other pharmaceutically active agents, including other CFTR-activating agents. The subject compounds may be used to provide an increase in the effectiveness of another chemical, such as a pharmaceutical (e.g., other CFTR-activating agents, or agents that affect-cellular misprocessing of mutant-CFTR), or a decrease in the amount of another chemical, such as a pharmaceutical (e.g., other CFTR-activating agents), that is necessary to produce the desired biological effect.

Examples of other CFTR activating agents include, but are not limited to, enhancers of intracellular cAMP levels, such as for example, but not limited to, forskolin, rolipram, 8-bromo-cAMP, theophylline, papaverine, cAMP and salts, analogs, or derivatives thereof. Other examples include beta agonists, tobramycin (TOBI®, Chiron Inc., Emeryville, Calif.) and curcumin (Eagan et al., (2004) Science 304:600-603).

The compounds described above may also be combined with other therapies for CF, including oral corticosteroids, ibuprofen, ribovarin or antibiotics such as dicloxacillin, cephalosporin, cephalexin, erythromycin, amoxicillin-clavulanate, ampicillin, tetracycline, tfimethoprim-sulfamethoxazole, chloramphenicol ciprofox-acin, tobramycin,. gentamicin, cephalosporins, monobactams and the like.

The compounds described herein for use in combination therapy with the compounds of the present invention may be administered by the same route of administration (e.g. intrapulmonary, oral, enteral, etc.) that the compounds are administered. In the alternative, the compounds for use in combination therapy with the compounds of the present invention may be administered by a different route of administration that the compounds are administered.

Kits

Kits with unit doses of the subject compounds, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Methods

Methods for Increasing Chloride Ion Permeability of a Mutant-CFTR Cell

The invention provides methods for increasing ion permeability of a cell that produces mutant-CFTR protein, with cells having ΔF508-CFTR being of particular interest. In general, the method involves contacting the cell with a compound in an amount effective to activate the mutant-CFTR protein and increase ion permeability of the cell. In one embodiment of particular interest, a compound of the invention is used in the method in combination with a second mutant-CFTR activator or potentiator.

In many embodiments, the cell mutant-CFTR protein is present on the plasma membrane of the cell.-Methods of detecting mutant-CFTR protein presence on the plasma membrane are well known in the art and can include but are not limited to, for example, labeling a molecule that binds to CFTR protein with a fluorescent, chemical or biological tag. Examples of molecules that bind to CFTR protein include, without limitation, antibodies (monoclonal and polyclonal), FAB fragments, humanized antibodies and chimeric antibodies. For an example of an antibody that binds to CFTR protein, see, e.g. U.S. Pat. No. 6,201,107.

In many embodiments, the cell has increased permeability to chloride ions, and the contacting of the cell with a compound of the invention, particularly when provided in combination with a mutant-CFTR activator or potentiator, increases the rate of chloride ion transport across the plasma membrane of the cell. Contacting the cell with a compound of the invention usually increases the activity of mutant-CFTR protein to increase ion transport.

In most embodiments, the ion transport activity of mutant-CFTR, or the permeability of a cell to ions, is increased by up to about 10%, by up to about 20%, by up to about 50%, by up to about 100%, by up to about 150%, by up to about 200%, by up to about 300%, by up to about 400%, by up to about 500%, by up to about 800%, or up to about 1000% or more. In certain embodiments, where there is no detectable ion transport activity of mutant-CFTR or permeability of a cell to ions, contacting of the cell with a compound of the invention causes detectable activity of mutant-CFTR or permeability of a cell to ions.

Activation of mutant-CFTR and/or ion permeability may be measured using any convenient methods that may use molecular markers, e.g., a halide sensitive GFP or another molecular marker (e.g., Galietta et al., (2001) *FEBS Lett.* 499, 220-224), patch clamp assays, and short circuit assays.

Suitable cells include those cells that have an endogenous or introduced mutant-CFTR gene. Suitable cells include mammalian cell systems (e.g., COS, CHO, BHK, 293, 3T3 cells etc.) harboring constructs that have an expression cassette for expression of mutant-CFTR. The cell used in the subject methods may be a cell present in vivo, ex vivo, or in vitro. As used herein, the term "expression cassette" is meant to denote a genetic sequence, e.g. DNA or RNA, that codes for mutant-CFTR protein, e.g., ΔF508-CFTR. Methods of introducing an expression cassette into a cell are well known in the art, see for example, Sambrook et al., *Molecular Cloning: A Laboratory Manual*. Cold Spring Harbor Laboratory Press, NY, Vol. 1, 2, 3 (1989).

Methods of Treating Cystic Fibrosis

The invention also provides methods of treating a subject having a condition associated with mutant-CFTR, e.g., cystic fibrosis. In general, the method involves administering to the subject a compound of the invention in an amount effective to activate a mutant-CFTR protein to increase ion transport and thereby treat the condition. In an embodiment of particular interest, a compound of the invention is administered in combination with a second mutant-CFTR activator or potentiator, e.g., a compound that enhances intracellular cAMP, e.g., forskolin.

The compounds disclosed herein are useful in the treatment of a mutant-CFTR-mediated condition, e.g., any condition, disorder or disease, or symptom of such condition, disorder, or disease, that results from the presence and/or activity of mutant-CFTR as compared to wild-type CFTR, e.g., activity of mutant-CFTR in ion transport. Such conditions, disorders, diseases, or symptoms thereof are amenable to treatment by activation of mutant-CFTR activity, e.g., activation of mutant-CFTR chloride transport. Cystic fibrosis, a hereditary condition associated with a mutant-CFTR, e.g., ΔF508-CFTR, is an example of a condition that is treatable using the compounds of the invention. Use of the compounds of the invention in combination with a second mutant CFTR activator or potentiator is of particular interest.

Cystic fibrosis is predominantly a disorder of infants, children and young adults, in which there is widespread dysfunction of the exocrine glands; characterized by signs of chronic pulmonary disease (due to excess mucus production in the respiratory tract), pancreatic deficiency, abnormally high levels of electrolytes in the sweat and occasionally by biliary cirrhosis. Also associated with the disorder is an ineffective immunologic defense against bacteria in the lungs.

Pathologically, the pancreas shows obstruction of the pancreatic ducts by amorphous eosinophilic concretions, with consequent deficiency of pancreatic enzymes, resulting in steatorrhoea and azotorrhoea and intestinal malabsorption. The degree of involvement of organs and glandular systems may vary greatly, with consequent variations in the clinical picture.

Nearly all exocrine glands are affected in cystic fibroses in varying distribution and degree of severity. Involved glands are of three types: those that become obstructed by viscid or solid eosinophilic material in the lumen (pancreas, intestinal glands, intrahepatic bile ducts, gallbladder, submaxillary glands); those that are histologically abnormal and produce an excess of secretions (tracheobronchial and Brunner's glands); and those that are histologically normal but secrete excessive sodium and chloride (sweat, parotid, and small salivary glands). Duodenal secretions are viscid and contain an abnormal mucopolysaecharide. Infertility occurs in 98% of adult men secondary to maldevelopment of the vas deferens or to other forms of obstructive azoospermia. In women, fertility is decreased secondary to viscid cervical secretions, but many women with CF have carried pregnancies to term. However, the incidence of maternal complications increases.

Fifty percent of cystic fibrosis patients with pulmonary manifestations usually chronic cough and wheezing associated with recurrent or chronic pulmonary infections. Cough is the most troublesome complaint, often accompanied by sputum, gagging, vomiting, and disturbed sleep. Intercostal retractions, use of accessory muscles of respiration, a barrel-chest deformity, digital clubbing, and cyanosis occur with disease progression. Upper respiratory tract involvement includes nasal polyposis and chronic or recurrent sinusitis. Adolescents may have retarded growth, delayed onset of puberty, and a declining tolerance for exercise. Pulmonary complications in adolescents and adults include pneumothorax, hemoptysis, and right heart failure secondary to pulmonary hypertension.

Pancreatic insufficiency is clinically apparent in 85 to 90% of CF patients, usually presents early in life, and may be progressive. Manifestations include the frequent passage of bulky, foul-smelling, oily stools; abdominal protuberance; and poor growth pattern with decreased subcutaneous tissue and muscle mass despite a normal or voracious appetite. Rectal prolapse occurs in 20% of untreated infants and toddlers. Clinical manifestations may be related to deficiency of fat-soluble vitamins.

Excessive sweating in hot weather or with fever may lead to episodes of hypotonic dehydration and circulatory failure. In arid climates, infants may present with chronic metabolic alkalosis. Salt crystal formation and a salty taste on the skin are highly suggestive of CF.

Insulin-dependent diabetes develops in 10% of adult patients having CF, and multilobular biliary cirrhosis with varices and portal hypertension develops in 4 to 5% of adolescents and adults. Chronic and/or recurrent abdominal pain may be related to intussusception, peptic ulcer disease, periappendiceal abscess, pancreatitis, gastroesophageal reflux, esophagitis, gallbladder disease, or episodes of partial intestinal obstruction secondary to abnormally viscid fecal contents. Inflammatory complications may include vasculitis and arthritis.

Any of above symptoms of CF may be treated using the compounds of the invention, with use of such compounds-in combination with a second mutant-CFTR activator or potentiator being of particular interest.

The above methods may be used to treat CF and its symptoms in humans or in animals. Several animal models for CF are known in the art. For example, Engelhardt et al. (*J. Clin. Invest.* 90: 2598-2607, 1992) developed an animal model of the human airway, using bronchial xenografts engrafted on rat tracheas and implanted into nude mice. More recently transgenic models of cystic fibrosis have been produced (e.g., Clarke et al., *Science* 257: 1125-1128, 1992; Dorin et al., *Nature* 359: 211-215, 1992). With the recent advances of nuclear transfer and stem cell transformation technologies, the alteration of a wild type CFTR gene in an animal to make it into a mutant-CFTR gene is possible for a wide variety of animals.

Many of these animal show human CF symptoms. In particular, many of these animals showed measurable defects in ion permeability of airway and intestinal epithelia, similar to those demonstrable in human CF tissues, and a susceptibility to bacterial infection. Furthermore, most of the deficient mice had intestinal pathology similar to that of meconium ileus. Also, there appeared to be no prenatal loss from litters produced from crosses between heterozygotes.

Animals suitable for treatment using the subject methods include any animal with a mutant-CFTR related condition, particularly-a mammal, e.g., non-human primates (e.g., monkey, chimpanzee, gorilla, and the like), rodents (e.g., rats, mice, gerbils, hamsters, ferrets, and the like), lagomorphs, swine (e.g., pig, miniature pig), equine, canine, feline, and the like. Large animals are of particular interest. Transgenic mammals may also be used, e.g. mammals that have a chimeric gene sequence. Methods of making transgenic animals are well known in the art, see, for example, U.S. Pat. No. 5,614,396. For an example of a transgenic mouse with a CFTR defect, see e.g. WO 94/04669.

Such animals may be tested in order to assay the activity and efficacy of the subject compounds. Improvement in lung function can be assessed by, for example, monitoring prior to and during therapy the subject's forced vital capacity (FVC), carbon monoxide diffusing capacity ($DL_{CO}$), and/or room air $pO_2$>55 mmHg at rest. Significant improvements in one or more of these parameters is indicative of efficacy. It is well within the skill of the ordinary healthcare worker (e.g., clinician) provide adjust dosage regimen and dose amounts to provide for optimal benefit to the patient according to a variety of factors (e.g., patient-dependent factors such as the severity of the disease and the like), the compound administered, and the like).

Subjects Suitable for Treatment

Subjects suitable for treatment with a method of the present invention include individuals having mutant-CFTR protein-mediated condition disorder or disease, or symptom of such condition, disorder, or disease that results from or is correlated to the presence of a mutant-CFTR, usually two alleles of the mutant CFTR. Moreover, subjects suitable for treatment with a method of the present invention include individuals with Cystic Fibrosis (CF). Of particular interest in many embodiments is the treatment of humans with CF.

Symptoms of mutant-CFTR protein-mediated conditions include meconium ileus, liver disease including biliary tract obstruction and stenosis, pancreatic insufficiency, pulmonary disease including chronic Pseudomonas aeruginosa infections and other infections of the lung, infertility associated with abnormal vas deferens development or abnormal cervical mucus, and carcinoma including adenocarcinoma.

The compounds of the present invention affects the ion transport capability of the mutant-CFTR by increasing the reduced level of ion transport mediated by a mutant-CFTR, such as the ΔF508-CFTR. As such, the compounds of the present invention have particular clinical utility in treating a subset of CF patients that have mutations in the CFTR gene that results a mutant-CFTR that is expressed in the plasma membrane and has reduced chloride conductance capability or has abnormal regulation of conductance. The compounds of the present invention also have clinical utility in treating CF patients when used in conjunction with compounds that correct cellular misprocessing of a mutant-CFTR, such as 4F508-CFTR.

CFTR mutations associated with CF are well known in the art. These mutations can be classified in five general categories with respect to the CFTR protein. These classes of CFTR dysfunction include limitations in CFTR production (e.g., transcription and/or translation) (Class I), aberrant folding and/or trafficking (Class II), abnormal regulation of conduction (Class III), decreases-in chloride conduction (Class IV), and reductions in synthesis (Class V). Due to the lack of functional CFTR, Class I, I, and III mutations are typically associated with a more severe phenotype in CF (i.e. pancreatic insufficiency) than the Class IV or V mutations, which may have very low levels of functional CFTR expression. A listing of the different mutations that have been identified in the CFTR gene is as found at the world wide website of the Cystic Fibrosis Mutation Database at genet.sickkids.on.ca/cgi-bin/WebObjects/MUTATION, specifically incorporated by reference herein in its entirety.

A subject suitable for treatment with a method of the present invention may be homozygous for a specific mutant-CFTR, i.e. homozygous subjects with two copies of a specific mutant-CFTR, e.g, ΔF508-CFTR In addition, subjects suitable for treatment with a method of the present invention may also be compound heterozygous for two different CFTR mutants, i.e., wherein the genome of the subjects includes two different mutant forms of CFTR, e.g., a subject with one copy of ΔF508-CFTR and a copy of different mutant form of CFTR.

In some embodiments of the invention, the mutant-CFTR polypeptide is ΔF508-CFTR. The invention, however, should not be construed to be limited solely to the treatment of CF patients having this mutant form of CFTR. Rather, the invention should be construed to include the treatment of CF patients having other mutant forms of CFTR with similar characteristics, that result in expression of the mutant-CFTR in the plasma membrane and has reduced chloride conductance capability or has abnormal regulation of conductance.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The following methods and materials are used in the examples below.

Cell Lines

Clonal populations of Fischer rat thyroid (FRT) epithelial cells stably co-expressing human ΔF508-CFTR and the high-sensitivity halide-sensing green fluorescent analog YFP-H148Q/I152L (Galietta et al., A.S. (2001) FEBS Lett. 499, 220-224) were generated by liposome transfection and limiting dilution with Zeocin/G418 selection. More than 100 clones were evaluated for high fluorescence and ΔF508-CFTR plasma membrane targeting after growth at 27° C. for 24 hours. For screening, cells were cultured on plastic in Coon's modified F12 medium supplemented with 10% fetal bovine serum, 2 mM L-glutamnine, 100 U/ml penicillin, and 100 μg/ml streptomycin, and plated on black 96-well microplates (Corning-Costar 3904) at 30,000 cells/well. For short-circuit measurements cells were cultured on Snapwell permeable supports (Corning-Costar) at 500,000 cells/insert. Some measurements were done using stably transfected FRT cells expressing YFP-H148Q and wildtype- or G551D-CFTR (Galietta et al., (2001) J. Biol. Chem. 276, 19723-19728). Patch clamp experiments were done on ΔF508-CFTR-expressing FRT cells plated in 35-mm Petri dishes.

Compounds

A collection of 100,000 diverse drug-like compounds (molecular sizes 350-550 daltons, purchased from ChemBridge Co.) was used for initial screening. For optimization, >1000 analogs of the compounds identified in the primary screen were purchased from ChemBridge or ChemDiv (out of ~600,000 available compounds) or synthesized/purified. Compounds were prepared as 10 mM stock solutions in DMSO. Secondary plates containing one or four compounds per well were prepared for screening (0.25 mM in DMSO). Compounds for secondary analysis were purified and confirmed by NMR and liquid chromatography/mass spectrometry.

Synthesis of Tetrahydrobenzothiophenes

Compounds with different $R_1$-substituents (FIG. 3A) were synthesized by first preparing the 2-aminotetrahydrobenzo[b]thlophene derivative by reaction of cyclohexanone and sulfur with 2-cyanoacetamide in the presence of diethylamine (Gewald et al., (1996) Chem. Ber. 99, 94-100). The product in pyridine was reacted with 2-chloro-benzoylchloride in benzene, extracted in benzene, and recrystallized in ethyl acetate-hexane (yields 70-80%). Structures were confirmed by NMR. Compound structures were confirmed by $^1$H NMR mass spectrometry.

Screening Procedures

Screening was carried out using a Beckman integrated system containing a 3-meter robotic arm, $CO_2$ incubator containing microplate carousel, plate-washer, liquid handling workstation, bar code reader, delidding station, plate sealer, and two FluoStar fluorescence plate readers (Galaxy, BMG Lab Technologies), each equipped with dual syringe pumps and HQ500/20X (500±10 nm) excitation and HQ535/30M (535±15 nm) emission filters (Chroma) (details in ref. 15). Software was written in VBA (Visual Basic-for Applications) to compute baseline-subtracted fluorescence slopes (giving halide influx rates).

For assay of ΔF508-CFTR potentiator activity the incubator (27° C., 90% humidity, 5% $CO_2$/95% air) was loaded with forty-to-sixty 96-well plates containing FRT cells. After an 18-24 hour incubation plates were washed 3 times with PBS (300 μl/wash) leaving 50 μl PBS. 10 μl of PBS containing 120 μM forskolin was added, and after 5 min test compounds (0.6 μl of 0.25 mM DMSO solution) were added to each well to give 2.5 μM final-compound concentrations. After 15 min, 96-well plates were transferred to a plate reader for fluorescence assay. Each well was assayed individually for $I^-$ influx by recording fluorescence continuously (200 ms per point) for 2 s (baseline) and then for 12 s after rapid (<1 s) addition of 160 μL of isosmolar PBS in which 137 mM $Cl^-$ was replaced by $I^-$. $I^-$ influx rates were computed from initial fluorescence versus time-curve slopes (determined by $3^{rd}$ order polynomial regression) after normalization for total fluorescence (background subtracted initial fluorescence).

Assays of cAMP and Phosphatase Activity cAMP activity was measured using the BIOTRAK enzymatic immunoassay (Amersham) on FRT cell lysates after incubation with the compound of interest for 10 min without or with 0.5 µM forskolin. Phosphatase activity was determined on cell homogenates using a non-radioactive assay kit (Promega) as described previously (Galietta et al., (2001) J. Biol. Chem. 276, 19723-19728).

Short-Circuit Current Measurements

Using chamber experiments were performed 7-9 days after plating ΔF508-CFTR expressing FRT cells on Snapwell inserts. The basolateral solution contained (in mM): 130 NaCl, 2.7 KCl, 1.5 KH$_2$PO$_4$, 1 CaCl$_2$, 0.5 MgCl$_2$, 10 glucose, 10 Na-Hepes (pH 7.3). In the apical bathing solution 65 mM NaCl was replaced by Na gluconate, and CaCl$_2$ was increased to 2 mM. Solutions were bubbled with air and maintained at 37° C. The basolateral membrane was permeabilized with 250 µg/ml amphotericin B. For human bronchial epithelial cells, apical and basolateral chambers contained 126 mM NaCl, 0.38 mM KH$_2$PO$_4$, 2.1 mM K$_2$HPO, 1 mM MgSO$_4$, 1 mM CaCl$_2$, 24 mM NaHCO$_3$, and 10 mM glucose (basolateral membrane not permeabilized). The hemichambers were connected to a DVC-1000 voltage clamp (World Precision Instruments) via Ag/AgCl electrodes and 1 M KCl agar bridges for recording short-circuit current Whole-Cell Patch-Clamp Cells were seeded at a density of $10^4$ cells/well and used 2-4 days after plating. Borosilicate glass pipettes were fire polished to obtain tip resistances of 2-4 MΩ. Currents were sampled at 500 Hz using a patch-clamp amplifier (EPC-7, List, Darmstadt) and low-pass filtered using a 4-pole Bessel filter set at a cutoff frequency of 250 Hz. The extracellular (bath) solution contained (in mM): 150 NaCl, 1 CaCl$_2$, 1 MgCl$_2$, 10 glucose, 10 mannitol, and 10 TES (pH 7.4). The pipette solution contained (in mM): 120 CsCl, 1 MgCl$_2$, 10 TEA-Cl, 0.5 EGTA, 1 Mg-ATP, and 10 Hepes (pH 7.3). Membrane conductances were monitored by alternating the membrane potential between +80 and −100 mV. Current-voltage relationships were generated by applying voltage pulses between −100 and +100 mV in 20 mV steps.

Analysis of ΔF508-CFTR Misprocessing

Cells were incubated at 37° C. in the presence of 10 µM ΔF508-CFTR potentiators. For functional studies, the plate reader assay was carried out at 15 min after washing potentiators, and adding forskolin (20 µM) and the potentiator ΔF508$_{act}$-02 (2 µM). For biochemical analysis of ΔF508-CFTR glycosylation, BHK cells expressing ΔF508-CFTR-HA (hemagglutinin-tagged, Sharma et al., (2001) J. Biol. Chem. 276, 8942-8950) were incubated with test compounds (10 µM) for 24 hrs at 37° C. Cells were lysed in RIPA buffer, proteins were separated by SDS-PAGE, transferred to nitrocellulose, and probed with M3A7 and L12B4 anti-CFTR antibody mixture or anti-Na/K-ATPase antibody.

Computational Analysis

Data manipulations, property calculations, and model building were performed using Pipeline Pilot (Scitegic, Inc., San Diego Calif.). The data set for modeling consisted of 3025 tetrahydrobenzothiophenes containing 40 active compounds. The Bayesian learning model contained the following parameters: molecular weight, surface area, polar surface area, number of H-bond donors, number of H-bond acceptors, AlogP, and Scitegic's functional class fingerprints with a diameter of 6 bonds (FCFP_6). The data set of 3025 tetrahydrobenzothiophenes was partitioned randomly into 4 sets of approximately equal size. The Bayesian learner was trained on 3 of the 4 data partitions to distinguish between active and inactive tetrahydrobenzothiophenes, producing 4 different models.

Each Bayesian model reduced information from the inputted parameters into a single dimension. The Mann-Whitney test for non-parametric two-group comparisons was used to assess the likelihood that the distributions of active and inactive tetrahydrobenzothiophenes represent different populations. Favorable and unfavorable structural elements were extracted from the learning models using Pipeline Pilot's Learned Property Viewer component. A congeneric series for structure-activity analysis was generated by removing the R-group from each active compound, and then using the resulting scaffold to perform a substructure search for inactive tetrahydrobenzothiophenes.

Example 1

Screening Assays

The high-throughput screen was designed to identify compounds that activated ΔF508-CFTR when expressed at the cell plasma membrane. FRT epithelial cells co-expressing ΔF508-CFTR and a high sensitivity green fluorescent protein-based halide indicator were incubated at 27° C. for 24 h to permit ΔF508-CFTR plasma membrane targeting (FIG. 1A). After washing, forskolin (20 µM) and test compounds (2.5 µM) were added to individual wells of 96-well plates. The I$^-$ influx assay was carried out ~15 min later by measurement of the time course of decreasing YFP fluorescence after creation of an inwardly-directed I$^-$ gradient. A high concentration of forskolin was used to identify ΔF508-CFTR potentiators that may interact directly with ΔF508-CFTR rather than alter cAMP concentration. Since activation of CFTR requires cAMP stimulation, forskolin, an enhancer of cAMP, was added to the in vitro models in order to mimic the cellular cAMP stimulation.

FIG. 1B (top curve) shows representative time course data from a control well ('saline') in which slow I$^-$ influx was seen when forskolin was added without test compounds. Examples of inactive compounds are shown. Each plate also contained positive control wells in which a dose-response was done for genistein, a known (though low potency) ΔF508-CFTR activator. Rapid I$^-$ influx was found for some of the 100,000 test compounds (bottom curves). FIG. 1C summarizes the results of the primary screen. While most compounds had no significant ΔF508-CFTR potentiating activity at 2.5 µM, there were 75 strong (I$^-$ influx>0.1 mM/s) and 252 weaker potentiators.

The strong potentiators were subjected to secondary analysis to select a subset for further analysis. None of the strong potentiators stimulated I$^-$ influx in the fluorescence assay using FRT null cells (expressing YFP-H148Q/Y152L alone) or in ΔF508-CFTR expressing cells in the absence of forskolin. The increased I$^-$ influx for each potentiator was blocked by the thiazolidinone CFTR inhibitor CFTR$_{inh}$-172 (19). Dose-response studies were done to determine K$_d$ and V$_{max}$, with representative data shown in FIG. 1D. Of the 75 strong potentiators with>0.1 mM/s I$^-$ influx in the primary screen (at 2.5 µM), there were 32 compounds with K$_d$<1 µM with V$_{max}$ greater than that of the reference compound genistein (at 50 µM). Several of these compounds are shown in FIG. 6, along with data as to the activity of these compounds.

Example 2

Short-Circuit Current Analysis

Figure 2B:
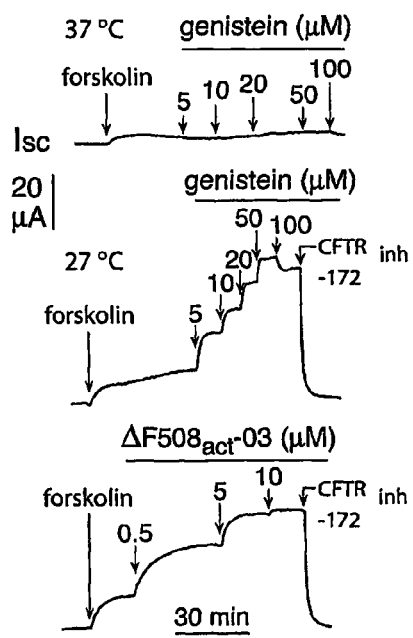
FIG. 2B. is three panels of graphs showing transepithelial short-circuit current (I$_{sc}$) in FRT cells expressing mutant-CFTR showing responses to 20 µM forskolin and genistein or ΔF508$_{act}$-05. Where indicated, the CMTR inhibitor CFTR$_{inh}$- 172 (5 µM) was added. Cells were cultured at 37° C. (top curve) or 27° C. (middle and bottom).

Short-circuit current analysis was done on each of these compounds to confirm bona fide activation of ΔF508-CFTR Cl⁻ currents. Experiments were done after basolateral membrane permeabilization and in the presence of a transepithelial Cl⁻ gradient, so that short-circuit current represents apical membrane Cl⁻ current. Representative data are shown in FIG. 2B. Thirteen compounds increased short-circuit current to levels comparable to that of maximal genistein, but with $K_d$<2 µM. None of the compound activated short-circuit current in FRT null cells or in ΔF508-CFTR expressing FRT cells in the absence of forskolin. Most of the strong potentiators of ΔF508-CFTR CF conductance belonged to 6 distinct structural classes, with the chemical structures of the most potent compound of each class shown in FIG. 2A. These six compounds and their respective structural classes were (1) 1-Furan-2-yhnethyl-5-[1-(4-methoxy-phenyl)-2,5-dimethyl-1H-pyrrol-3-ylmethylene]-pyrimidine-2,4,6-trione (ΔF508$_{act}$-01) ("pyrimidinetrione")

(2) 2-(2-Chloro-benzoylamino)-4,5,6,7-tetrahydro-benzo[b]thiophene-3-carboxylic acid amide (ΔF508$_{act}$-02) ("tetrahydrobenzothiophenes");

(3) 8-Bromo-6-methyl-2,3,4,9-tetrahydro-carbazol-1-one (ΔF508$_{act}$-03) ("tetrahydrocarbazols");

(4) 2-Amino-1-(4-tert-butyl-phenoxy)-anthraquinone (ΔF508$_{act}$-04) ("anthraquinone");

(5) 4-(4-Isopropyl-phenyl)-2,6-dimethyl-1,4-dihydro-pyridine-3,5-dicarboxylic acid dimethyl ester (ΔF508$_{act}$-05) ("dihydropyridine"); and (6) 3-Benzoylamino-benzofuran-2-carboxylic acid amide (ΔF508$_{act}$-06) ("benzofuran").

Compounds similar to class '03' potentiators (ΔF508$_{act}$-03) were identified in a previous screening for activity in promoting ion transport of wildtype CFTR (Ma et al., (2002) *J. Biol. Chem.* 277, 37235-37241; specifically incorporated by reference herein in its entirety), while the other classes represent novel scaffolds for CFTR activators. Interestingly, four of the compounds producing strong halide influx in the fluorescence assay did not produce Cl⁻ currents by short-circuit current analysis, suggesting that they may induce electroneutral halide transport through ΔF508-CFTR.

Example 3

Patch-Clamp Analysis

Figure 2C:
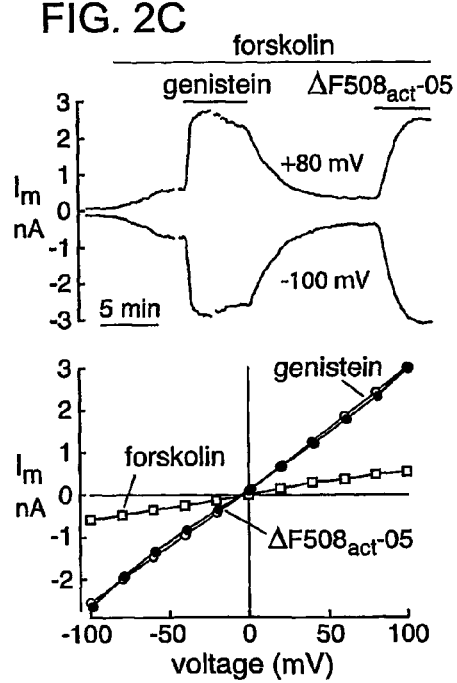
FIG. 2C. is two panels of graph showing activation of membrane currents at +80 and −100 mV in a voltage-clamped cell by genistein (50 µM) and ΔF508$_{act}$-05 (5 µM) in the presence of forskolin (20 µM) (top panel). Current-voltage relationships after activation by forskolin alone or forskolin+genistein or ΔF508$_{act}$-05 (bottom panel).

To assess the characteristics of the channels activated by ΔF508-CFTR potentiators, whole-cell recordings were done using the patch-clamp technique. FIG. 2C (top) shows membrane currents after forskolin alone and then forskolin with genistein demonstrating again the gating defect. After genistein washout, a ΔF508-CFTR potentiator gave similar membrane current. Current-voltage relationships generated in the presence of genistein or ΔF508-potentiators had the same linear ohmic behavior (FIG. 2C, bottom) as that found for activated wildtype CFTR. The currents showed no relaxation phenomena at positive or negative membrane potentials, providing evidence against the involvement of volume-sensitive or Ca$^{2+}$-activated Cl⁻ channels.

The six ΔF508-CFTR potentiators shown in FIG. 2A were tested for activation of wildtype and G551D-CFTR in transfected FRT cells. None of the compounds gave measurable G551D-CFTR activation at 10 µM in the presence of 20 µM forskolin, whereas strong activation was found for the positive control (50 µM genistein+20 µM forskolin). All ΔF508-CFTR potentiators activated wildtype CFTR, but only in the presence of a low concentration of forskolin (50 nM) which did not itself activate CFTR. $K_d$ values for activation of wildtype CFTR by ΔF508$_{act}$-01 through ΔF508$_{act}$-06 were (in µM): 0.18±0.02, 1.3±0.2, 2.2±0.3, 0.02±0.005, 0.06±0.01 and 0.05±0.01, respectively. These potencies are quite different from those for ΔF508-CFTR activation. For comparison, $K_d$ values for activation of ΔF508-CFTR by ΔF508$_{act}$-01 through ΔF508$_{act}$-06 from the fluorescence assay were (in µM): 1.3±0.1, 0.18±0.03, 0.70±0.04, 0.87±0.1, 0.10±0.01 and 0.65±0.08, respectively.

Example 4

Secondary Screens

A secondary library of >1000 compounds with structural similarity to each class of ΔF508-CFTR potentiators was screened to establish structure-activity relationships and to identify the best compounds for further analysis. Structural analogs of the benzofira, pyrimidinetrione, dihydropyridine and anthraquinone classes with good ΔF508-CFTR activating potencies were not identified. However 17 tetrahydrobenzothiophenes (class 02) were identified as giving good ΔF508-CFTR activation. The $K_d$ and $V_{max}$ of the six strongest ΔF508-CFTR potentiators are summarized in FIG. 3A. Further analysis showed rapid ΔF508-CFTR activation (FIG. 3B, left), with half-maximal activation in <3 min. Activation was fully reversed for most of the compounds at 60 min after washout (FIG. 3B, right). ΔF508-CFTR activation required low concentrations of forskolin (FIG. 3C).

Example 5 cAMP Stimulation, Phosphatase Inhibition and Other Assays

Figure 3A:
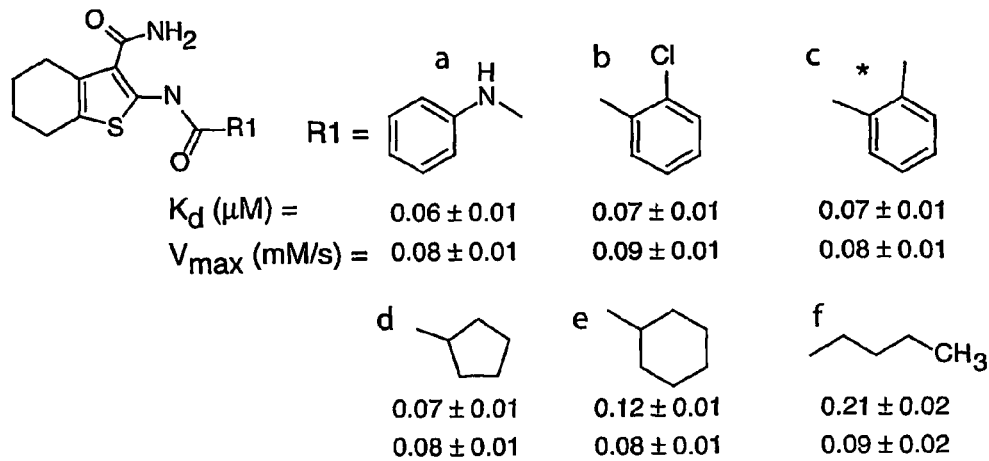
FIG. 3A. shows the chemical structure and I$^-$ influx dose-response data for six of the most potent substituted thiophene compounds.
Figure 3B:
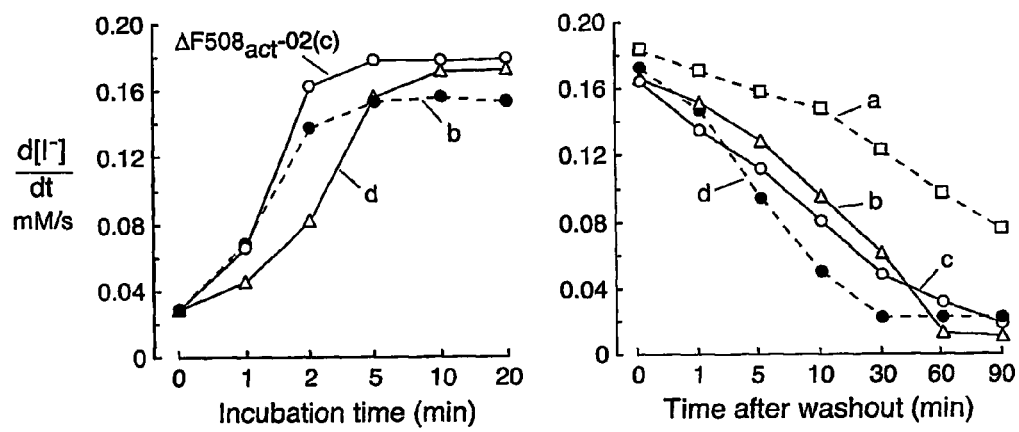
FIG. 3B. is a panel of two graphs showing kinetics of ΔF508-CFTR activation (left) and reversal after washout (right) for indicated compounds. In reversal studies, the compounds were incubated with cells for 5 min before washout.
Figure 3C:
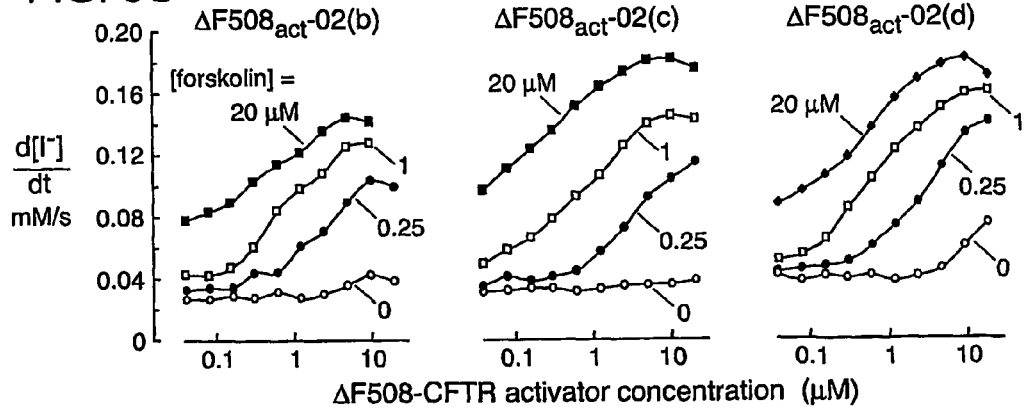
FIG. 3C. is a panel of three graphs showing forskolin dependence of mutant-CFTR activation. Concentration-activity data shown for indicated compounds at forskolin concentrations of 0, 0.25, 1 and 20 µM.

The compounds shown in FIGS. 2A and 3A were assayed for cAMP stimulation and phosphatase inhibition. Cellular cAMP content was measured in FRT cells in the presence of a low forskolin concentration (0.5 µM) with or without test compounds. As positive controls, a phosphodiesterase inhibitor (isobutylmethylxanthine (IBMX), 50 µM) and a cAMP-elevating CFTR activator (CFTR$_{act}$-16, 5 µM; ref. 15) strongly increased cAMP content from 129±7 to 1110±56 and 1733±51 finol/well, respectively. Maximal forskolin (20 µM) gave 1350±17 finol/well. The ΔF508 potentiators at 5 µM gave no increase in cellular cAMP content, except for ΔF508$_{act}$-04 and ΔF508$_{act}$-06, which gave modest cAMP elevations (212±17 and 281±37 finol/well, respectively). Phosphatase assay showed no inhibition of phosphatase activity by the ΔF508 potentiators under conditions where the known phosphatase inhibitor okadaic acid inhibited phosphatase activity by >90% (from 703±69 to 56±15 pmol free phosphate/µg protein). The ΔF508-CFTR potentiators (25 µM, 48 h) were judged to be non-toxic to FRT cells by the dihydrorhodamine assay (Wang et al., (2000) *J. Physiol.* 524: 637-638) and by unimpaired cell growth.

Figure 4A:
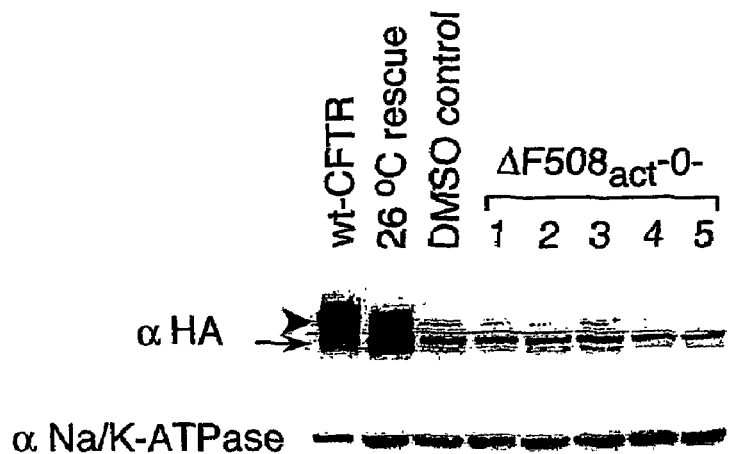
FIG. 4A. is a gel blot showing measurements of mutant-CFTR glycosylation in ΔF508-CFTR-HA expressing BHK cells. Immunoblot analyses on cell lysates were done using anti-HA (top) and anti-Na/K ATPase antibodies (bottom). Where indicated (26° C. rescue) cells were incubated at 26° C. for 24 hrs. Arrow, core-glycosylated CFTR; arrowhead, complex-glycosylated CFTR; wt-CFTR, human wild type CFTR-HA.
Figure 4B:
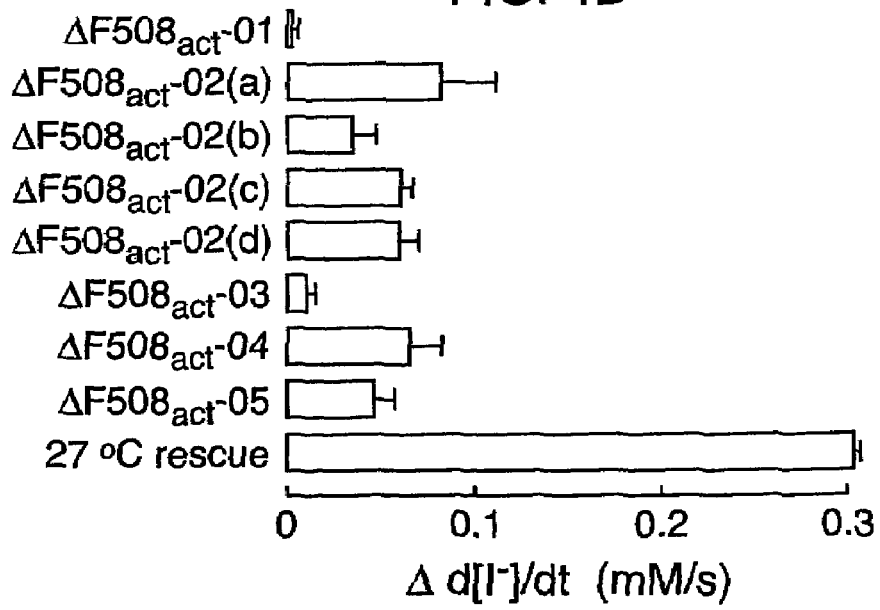
FIG. 4B. is a bar graph showing mutant-CFTR function measured using the plate reader assay (the same assay as used for in FIG. 1B) in which I$^-$ influx was measured after adding the compounds (10 µM) and forskolin (20 µM). Compounds (10 µM) were incubated with cells for 24 h at 37° C.

Because the ΔF508-CFTR potentiators probably activate plasma membrane-targeted ΔF508-CFTR by a direct interaction mechanism, the compounds were tested to determine whether they might correct ΔF508-CFTR cellular misprocessing (retention at endoplasmic reticulum). The ΔF508-CFTR expressing FRT cells were incubated for 24 h at 37° C. with the potentiators (10 µM). Plasma membrane ΔF508-CFTR was assessed biochemically and functionally. FIG. 4A shows core- and complex-glycosylated forms for wild type CFTR and for ΔF508-CFTR after 26° C. rescue. Little or no complex-glycosylated ΔF508-CFTR (C-band) was found after incubation of cells with the potentiators for 24 hrs at 37° C. Similar results were obtained on ΔF508-CFTR expressing FRT cells (data not shown). For functional assay, cells were washed after 24 h and I⁻ influx was measured 1-5 min after addition of forskolin (20 μM) and the strong potentiator ΔF508$_{act}$-02 (2 μM). FIG. 4B shows little increase in the rate of I⁻ influx (Δd[I⁻]/dt) by the potentiators, with positive 27° C. rescue control.

Example 6

Short Circuit Current Analysis

Figure 7:
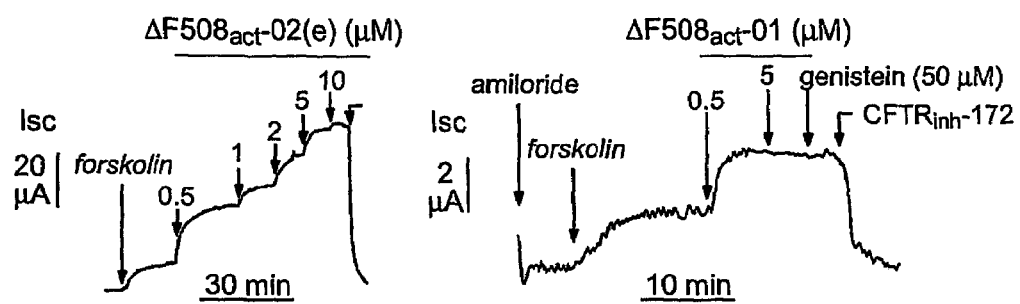
FIG. 7. shows representative short-circuit current experiments showing activation of Cl$^-$ currents in mutant-CFTR-expressing FRT cells (left panel) and human bronchial epithelia (right panel) by the indicated mutant-CFTR potentiators. Measurements were done at 37° C.

FIG. 7 shows that the tetrahydrobenzothiophene compounds induced strong Cl⁻ currents in short-circuit experiments with submicromolar activating potencies, both in temperature-rescued ΔF508-CFTR-expressing FRT cells (left panel) and human bronchial epithelial cells (right panel). The mean increase in short-circuit current ($I_{sc}$) was 1.2±0.1 μA/cm² in the human cells (S.E., n=25). In five sets of measurements on the human bronchial cells, the percentage increase in $I_{sc}$ after compound versus forskolin alone was 174±28 (genistein); percentages for ΔF508$_{act}$-01 through ΔF508$_{act}$-06 were (S.E., n=3-5): 174±34, 131±35, 40±11, 51±17, 107±42, and 104±35, respectively.

Example 7

Molecular Modeling and Validation of Model

A model relating activity to structural and calculated physical chemical parameters of the tetrahydrobenzothiophene class of ΔF508-CFTR potentiators was generated using a Bayesian learning methodology. The extracted minimal consensus substructure and physical properties of active tetrahydrobenzothiophenes are shown in FIG. 5A. The substructure allows for variation in the composition of the ring fused to the tetrahydrobenzothiophene and the group appended to the nitrogen at the 2-position of the tetrahydrobenzothiophene, but requires an amide at the 3-position and an amide or weakly basic group at the 2-position. The physical properties of the active subset of tetrahydrobenzothiophenes were clearly different from those of the full set of tetrahydrobenzothiophenes in the screening library (FIG. 5B). They also represent a distinct subset of the classic Lipinski parameters. The number of hydrogen bond donors and acceptors was low (<3 each), and the overall polar surface (72≦Å²≦98) and AlogP (2.3 to 3.6) fell within a narrow range. The learning model was successfully trained to distinguish between active and inactive tetrahydrobenzothiophenes and was cross-validated (4 data partitions, p<0.00001, regardless of originating training set) (FIG. 5C).

Further analysis of structure-activity trends was carried out by extracting the fingerprints from the active and inactive sets in the learned model, partitioning them into congeneric series, and examining the trends. FIG. 5D shows favorable and unfavorable structural elements identified by the Bayesian learning model from analysis of Scitegic functional class fingerprints. FIG. 5E illustrates a structure-activity series derived from the screening data. The seminal structural features of the model include: a) presence of a 4,5-fused tetrahydrobenzothiophene with the fused ring being a 6 or 7-membered aliphatic ring, b) presence of an unsubstituted carboxamide in the 3-position, and c) a high population of aromatic amides at the 2-position.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. A method of increasing halide ion permeability of a cell producing a ΔF508-CFTR protein, said method comprising contacting said cell with a substituted thiophene compound in an amount effective to increase ion permeability of said cell, wherein said compound has the formula:

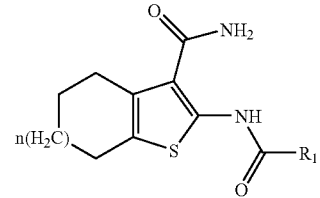

wherein n is 1 or 2, and R₁ is a phenyl group substituted with one to two substituents selected from halogen, methyl, amino, and nitro.

2. The method of claim 1, wherein said ion is a chloride ion or an iodide ion.

3. The method of claim 2, wherein said ΔF508-CFTR protein is present at a plasma membrane of said cell.

4. The method of claim 1, wherein said cell contains a recombinant expression cassette that encodes said ΔF508 CFTR protein.

5. The method of claim 1, wherein said cell contains a genome that encodes said ΔF508-CFTR protein.

6. The method of claim 1, wherein said compound increases ion transporting activity of said ΔF508-CFTR protein.

7. The method of claim 6, wherein said ion transporting activity increases a rate of transport of ions across a plasma membrane of said cell.

8. The method of claim 1, wherein the compound is together with at least one of a pharmaceutically acceptable carrier, a pharmaceutically acceptable diluent, a pharmaceutically acceptable excipient and a pharmaceutically acceptable adjuvant.

9. The method of claim 1, wherein R₁ has molecular weight of 58-165 Da.

10. The method of claim 8, wherein the compound is provided in a composition that does not contain detectable dimethyl sulfoxide.

11. The method of claim 1, wherein the compound is 2-(2-Chloro-benzoylamino)-4,5,6,7-tetrahydro-benzo thiophene-3-carboxylic acid amide or a pharmaceutically acceptable salt thereof.

12. The method of claim 1, wherein the phenyl group is substituted with halogen.

13. The method of claim 1, wherein the phenyl group is substituted with methyl.

14. The method of claim 1, wherein the phenyl group is substituted with amino.

15. The method of claim 1, wherein the phenyl group is substituted with nitro.

16. A method of increasing chloride ion permeability of a cell producing a ΔF508-CFTR protein, said method comprising
contacting said cell with a substituted thiophene compound in an amount effective to increase ion permeability of said cell,
wherein said compound has the formula:

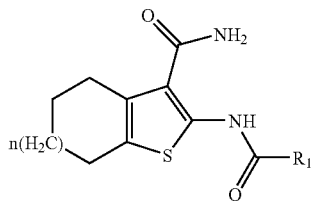

wherein n is 1 or 2, and $R_1$ is a phenyl group substituted with one to two substituents selected from halogen, methyl, amino, and nitro;
wherein said contacting is effective in increasing chloride ion permeability of the cell.

17. The method of claim 16, wherein said ΔF508-CFTR protein is present at a plasma membrane of said cell.

18. The method of claim 16, wherein said cell contains a recombinant expression cassette that encodes said ΔF508 CFTR protein.

19. The method of claim 16, wherein said cell contains a genome that encodes said ΔF508-CFTR protein.

20. The method of claim 16, wherein said compound increases ion transporting activity of said ΔF508-CFTR protein.

21. The method of claim 16, wherein the compound is together with at least one of a pharmaceutically acceptable carrier, a pharmaceutically acceptable diluent, a pharmaceutically acceptable excipient and a pharmaceutically acceptable adjuvant.

22. The method of claim 21, wherein the compound is provided in a composition that does not contain detectable dimethyl sulfoxide.

23. The method of claim 16, wherein $R_1$ has molecular weight of 58-165 Da.

24. The method of claim 16, wherein the compound is 2-(2-Chloro-benzoylamino)-4,5,6,7-tetrahydro-benzo thiophene-3-carboxylic acid amide or a pharmaceutically acceptable salt thereof.

25. The method of claim 16, wherein the phenyl group is substituted with halogen.

26. The method of claim 16, wherein the phenyl group is substituted with methyl.

27. The method of claim 16, wherein the phenyl group is substituted with amino.

28. The method of claim 16, wherein the phenyl group is substituted with nitro.

* * * * *

UNITED STATES PATENT AND TRADEMARK OFFICE
CERTIFICATE OF CORRECTION

| | |
|---|---|
| PATENT NO. | : 7,696,244 B2 |
| APPLICATION NO. | : 10/556195 |
| DATED | : April 13, 2010 |
| INVENTOR(S) | : Alan S. Verkman |

Page 1 of 1

It is certified that error appears in the above-identified patent and that said Letters Patent is hereby corrected as shown below:

Please replace the Statement Regarding Federally Sponsored Research beginning on column 1, line 16, with the following revised statement:

GOVERNMENT RIGHTS

--This invention was made with government support under grant nos. HL73856, EB00415, HL59198, EY13574, and DK35124 awarded by the National Institutes of Health. The government has certain rights in this invention.--

Signed and Sealed this

Tenth Day of August, 2010

David J. Kappos
*Director of the United States Patent and Trademark Office*